(12) United States Patent
Quintero et al.

(10) Patent No.: US 11,504,446 B2
(45) Date of Patent: Nov. 22, 2022

(54) SKIN CLOSURE DEVICES WITH SELF-FORMING EXUDATE DRAINAGE CHANNELS

(71) Applicant: Ethicon, Inc., Somerville, NJ (US)

(72) Inventors: Julian Quintero, Flemington, NJ (US); Leo B. Kriksunov, Ithaca, NY (US)

(73) Assignee: Ethicon, Inc., Raritan, NJ (US)

( * ) Notice: Subject to any disclaimer, the term of this patent is extended or adjusted under 35 U.S.C. 154(b) by 927 days.

(21) Appl. No.: 15/496,389

(22) Filed: Apr. 25, 2017

(65) Prior Publication Data

US 2018/0303967 A1      Oct. 25, 2018

(51) Int. Cl.
| | |
|---|---|
| *A61F 13/02* | (2006.01) |
| *A61L 15/58* | (2006.01) |
| *A61L 15/22* | (2006.01) |
| *A61L 15/42* | (2006.01) |
| *A61L 24/04* | (2006.01) |

(52) U.S. Cl.
CPC ............ *A61L 15/58* (2013.01); *A61F 13/025* (2013.01); *A61F 13/0253* (2013.01); *A61L 15/22* (2013.01); *A61L 15/425* (2013.01); *A61L 24/04* (2013.01)

(58) Field of Classification Search
CPC .... A61F 13/02; A61F 13/025; A61F 13/0253; A61L 15/22; A61L 15/425; A61L 15/58; A61L 24/04
USPC .............................................. 602/47, 55, 59
See application file for complete search history.

(56) References Cited

U.S. PATENT DOCUMENTS

| | | |
|---|---|---|
| 167,162 A | 8/1875 | French |
| 1,656,199 A | 1/1928 | Ensley |
| 2,399,545 A | 4/1946 | Davis |
| 2,508,855 A | 5/1950 | Brown |
| 2,721,858 A | 10/1955 | Joyner et al. |
| 2,722,220 A | 11/1955 | Mestrand |
| 2,807,262 A | 9/1957 | Lew |
| 2,905,174 A | 5/1959 | Smith |
| 3,085,572 A | 4/1963 | Blackford |

(Continued)

FOREIGN PATENT DOCUMENTS

| | | |
|---|---|---|
| CA | 2262408 | 8/2000 |
| CN | 1697639 A | 11/2005 |

(Continued)

OTHER PUBLICATIONS

3M™ Steri-Strip Adhesive Closures Product Catalog Brochure, (2011) 4 pages.

(Continued)

*Primary Examiner* — Keri J Nelson

(57) ABSTRACT

A device for application onto wounds with a liquid rapidly polymerizable adhesive for forming skin closure systems, comprising a thin flexible flat porous tape, preferably a mesh, elongated along a longitudinal axis and having a lower side or wound-facing side and an opposing upper side, a periphery, and central portion in immediate vicinity of the axis; said tape coated or impregnated with an initiator or accelerator of polymerization; said tape having a plurality of elongated traces of soluble pressure sensitive adhesive (PSA) disposed on the wound-facing side; said traces covering from about 3% to about 50% of area of said tape and extending from the periphery to the central portion of said tape.

14 Claims, 8 Drawing Sheets

(56) References Cited

U.S. PATENT DOCUMENTS

| | | |
|---|---|---|
| 3,254,111 A | 5/1966 | Hawkins et al. |
| 3,402,716 A | 9/1968 | Baxter |
| 3,520,300 A | 7/1970 | Flower, Jr. |
| 3,731,683 A | 5/1973 | Zaffaroni |
| 3,888,247 A | 6/1975 | Stenvall |
| 3,940,362 A | 2/1976 | Overhults |
| 3,983,878 A | 10/1976 | Kawchitch |
| 3,995,641 A | 12/1976 | Kronenthal et al. |
| 4,068,664 A | 1/1978 | Sharp et al. |
| 4,080,348 A | 3/1978 | Korpman |
| 4,126,130 A | 11/1978 | Cowden et al. |
| 4,140,115 A | 2/1979 | Schonfeld |
| 4,263,906 A | 4/1981 | Finley |
| 4,313,865 A | 2/1982 | Teramoto et al. |
| 4,340,043 A | 7/1982 | Seymour |
| 4,364,876 A | 12/1982 | Kimura et al. |
| 4,390,519 A | 6/1983 | Sawyer |
| 4,460,369 A | 7/1984 | Seymour |
| 4,560,723 A | 12/1985 | Millet et al. |
| 4,584,355 A | 4/1986 | Blizzard et al. |
| 4,585,836 A | 4/1986 | Homan et al. |
| 4,591,622 A | 5/1986 | Blizzard et al. |
| 4,612,230 A | 9/1986 | Liland et al. |
| 4,614,183 A | 9/1986 | McCracken et al. |
| 4,630,603 A | 12/1986 | Greenway |
| 4,655,767 A | 4/1987 | Woodard et al. |
| 4,671,266 A | 6/1987 | Legnyel et al. |
| 4,720,513 A | 1/1988 | Kameyama et al. |
| 4,728,380 A | 3/1988 | Jones et al. |
| 4,733,659 A | 3/1988 | Edenbaum et al. |
| 4,767,401 A | 8/1988 | Seiderman |
| 4,793,887 A | 12/1988 | Card et al. |
| 4,793,888 A | 12/1988 | Card et al. |
| 4,795,435 A | 1/1989 | Steer et al. |
| 4,852,571 A | 8/1989 | Gadsby et al. |
| 4,867,747 A | 9/1989 | Yarger |
| 4,872,450 A | 10/1989 | Austad |
| 4,950,282 A | 8/1990 | Beisang et al. |
| 4,966,605 A | 10/1990 | Thieler |
| 4,999,235 A | 3/1991 | Lunn et al. |
| 5,035,687 A | 7/1991 | Sandbank |
| 5,059,424 A | 10/1991 | Cartmell et al. |
| 5,086,763 A | 2/1992 | Hathman |
| 5,088,483 A | 2/1992 | Heinecke |
| 5,106,362 A | 4/1992 | Gilman |
| 5,125,907 A | 6/1992 | Philpott |
| 5,164,444 A | 11/1992 | Bernard |
| 5,173,302 A | 12/1992 | Holmblad et al. |
| 5,232,958 A | 8/1993 | Mallya et al. |
| 5,254,132 A | 10/1993 | Barley et al. |
| 5,259,835 A | 11/1993 | Clark et al. |
| 5,266,371 A | 11/1993 | Sugii et al. |
| D347,059 S | 5/1994 | Mota |
| 5,308,313 A | 5/1994 | Karami et al. |
| 5,328,687 A | 7/1994 | Leung et al. |
| 5,336,209 A | 8/1994 | Porzilli |
| 5,415,626 A | 5/1995 | Goodman et al. |
| 5,429,592 A | 7/1995 | Jensen |
| 5,445,597 A | 8/1995 | Clark et al. |
| 5,449,340 A | 9/1995 | Tollini |
| D363,126 S | 10/1995 | Dusek |
| 5,456,660 A | 10/1995 | Reich et al. |
| 5,476,440 A | 12/1995 | Edenbaum |
| 5,486,547 A | 1/1996 | Matsuda et al. |
| D370,258 S | 5/1996 | Newman |
| D373,750 S | 9/1996 | Gunderson |
| 5,571,079 A | 11/1996 | Bello et al. |
| 5,575,997 A | 11/1996 | Leung et al. |
| 5,582,834 A | 12/1996 | Leung et al. |
| 5,599,858 A | 2/1997 | Buchanan et al. |
| 5,620,702 A | 4/1997 | Podell et al. |
| 5,623,011 A | 4/1997 | Bernard |
| 5,624,669 A | 4/1997 | Leung et al. |
| D382,343 S | 8/1997 | Wandell et al. |
| 5,653,769 A | 8/1997 | Barley, Jr. et al. |
| D383,211 S | 9/1997 | Dunshee et al. |
| 5,662,599 A | 9/1997 | Reich et al. |
| D387,169 S | 12/1997 | Dunshee et al. |
| D389,244 S | 1/1998 | Dunshee et al. |
| 5,705,551 A | 1/1998 | Sasaki et al. |
| D391,639 S | 3/1998 | Dunshee et al. |
| 5,749,895 A | 5/1998 | Sawyer et al. |
| 5,762,955 A | 6/1998 | Smith |
| 5,780,048 A | 7/1998 | Lee |
| 5,782,788 A | 7/1998 | Widemire |
| 5,823,983 A | 10/1998 | Rosofsky et al. |
| 5,823,986 A | 10/1998 | Peterson |
| D402,371 S | 12/1998 | Haynes et al. |
| D403,425 S | 12/1998 | Hinds et al. |
| D404,139 S | 1/1999 | Young |
| 5,861,348 A * | 1/1999 | Kase ............... A61F 13/025 442/184 |
| 5,876,745 A | 3/1999 | Muraoka et al. |
| 5,902,443 A | 5/1999 | Kanakubo et al. |
| 5,928,611 A | 7/1999 | Leung |
| 5,931,800 A | 8/1999 | Rasmussen et al. |
| 5,947,917 A | 9/1999 | Carté et al. |
| 5,951,505 A | 9/1999 | Gilman et al. |
| 5,998,694 A | 12/1999 | Jensen et al. |
| D424,699 S | 5/2000 | Allen |
| 6,093,465 A | 7/2000 | Gilchrist et al. |
| 6,125,265 A | 9/2000 | Yamamoto et al. |
| 6,140,548 A | 10/2000 | Hansen et al. |
| 6,143,352 A | 11/2000 | Clark et al. |
| 6,155,265 A | 12/2000 | Hammerslag |
| 6,183,593 B1 | 2/2001 | Narang et al. |
| D439,973 S | 4/2001 | Choksi |
| 6,217,603 B1 | 4/2001 | Clark et al. |
| 6,238,692 B1 | 5/2001 | Smith |
| 6,245,960 B1 | 6/2001 | Eaton |
| 6,284,941 B1 | 9/2001 | Cox et al. |
| 6,310,166 B1 | 10/2001 | Hickey et al. |
| 6,329,564 B1 | 12/2001 | Lebner |
| 6,352,704 B1 | 3/2002 | Nicholson et al. |
| D458,687 S | 6/2002 | Dale et al. |
| 6,410,818 B1 | 6/2002 | Oyaski |
| 6,439,789 B1 | 8/2002 | Balance et al. |
| D463,564 S | 9/2002 | Siegwart et al. |
| 6,455,064 B1 | 9/2002 | Narang et al. |
| 6,479,725 B1 | 11/2002 | Brothers |
| 6,482,431 B2 | 11/2002 | Smith |
| 6,512,023 B1 | 1/2003 | Malofsky et al. |
| D471,984 S | 3/2003 | Dunshee et al. |
| D472,319 S | 3/2003 | Oltmann |
| 6,559,350 B1 | 5/2003 | Tetreault et al. |
| 6,579,469 B1 | 6/2003 | Nicholson et al. |
| 6,582,713 B2 | 6/2003 | Newell et al. |
| D477,076 S | 7/2003 | Wall |
| 6,589,269 B2 | 7/2003 | Zhu et al. |
| 6,595,940 B1 | 7/2003 | D'Alessio et al. |
| 6,596,917 B2 | 7/2003 | Oyaski |
| 6,599,318 B1 | 7/2003 | Gabbay |
| 6,620,846 B1 | 9/2003 | Jonn et al. |
| D480,879 S | 10/2003 | Boehm et al. |
| 6,632,450 B1 | 10/2003 | Gregory |
| 6,635,272 B2 | 10/2003 | Leaderman |
| 6,652,559 B1 | 11/2003 | Tetreault et al. |
| 6,667,051 B1 | 12/2003 | Gregory |
| 6,712,839 B1 | 3/2004 | Lönne |
| 6,787,682 B2 | 9/2004 | Gilman |
| 6,837,027 B2 | 1/2005 | Hickey |
| 6,841,716 B1 | 1/2005 | Tsutsumi |
| 6,942,683 B2 | 9/2005 | Dunshee |
| D515,701 S | 2/2006 | Horhota et al. |
| D516,728 S | 3/2006 | Wall |
| D520,639 S | 5/2006 | Dodd et al. |
| 7,041,124 B2 | 5/2006 | Purcell |
| 7,044,982 B2 | 5/2006 | Milbocker |
| 7,066,934 B2 | 6/2006 | Kirsch |
| 7,122,712 B2 | 10/2006 | Lutri et al. |
| 7,144,390 B1 | 12/2006 | Hannigan et al. |
| 7,164,054 B2 | 1/2007 | Mori et al. |
| D548,348 S | 8/2007 | Nash |
| 7,252,837 B2 | 8/2007 | Guo et al. |

(56) References Cited

U.S. PATENT DOCUMENTS

| | | |
|---|---|---|
| D562,461 S | 2/2008 | Nash et al. |
| 7,371,400 B2 | 5/2008 | Borenstein et al. |
| D574,962 S | 8/2008 | Atkins et al. |
| D580,553 S | 11/2008 | Nash |
| D581,467 S | 11/2008 | Winningham et al. |
| 7,457,667 B2 | 11/2008 | Skiba |
| D582,561 S | 12/2008 | Sachi |
| D584,415 S | 1/2009 | Sachi |
| 7,576,257 B2 | 8/2009 | LaGreca, Sr. |
| D611,156 S | 3/2010 | Dunshee |
| 7,713,463 B1 | 5/2010 | Reah et al. |
| D618,810 S | 6/2010 | Tanigawa et al. |
| D621,052 S | 8/2010 | Kase |
| D621,053 S | 8/2010 | Kase |
| D624,190 S | 9/2010 | Neri |
| D632,398 S | 2/2011 | Bray et al. |
| D636,881 S | 4/2011 | Clemens et al. |
| 7,943,811 B2 | 5/2011 | Da Silva Macedo, Jr. |
| 7,981,136 B2 | 7/2011 | Weiser |
| 7,982,087 B2 | 7/2011 | Greener et al. |
| D646,789 S | 10/2011 | Barth |
| 8,343,606 B2 | 1/2013 | Marchitto et al. |
| 8,353,966 B2 | 1/2013 | Day et al. |
| D676,490 S | 2/2013 | Bratter et al. |
| 8,372,051 B2 | 2/2013 | Scholz et al. |
| D679,098 S | 4/2013 | Ogawa |
| D679,402 S | 4/2013 | Conrad-Vlasak et al. |
| D679,403 S | 4/2013 | Heinecke et al. |
| D679,405 S | 4/2013 | Arbesman |
| D679,819 S | 4/2013 | Peron |
| D679,820 S | 4/2013 | Peron |
| D685,484 S | 7/2013 | Brambilla |
| 8,528,730 B2 | 9/2013 | Grossman |
| D691,730 S | 10/2013 | Smith et al. |
| D692,566 S | 10/2013 | Adoni |
| D693,010 S | 11/2013 | Mosa et al. |
| D694,892 S | 12/2013 | Chan et al. |
| 8,603,053 B2 | 12/2013 | Riesinger |
| D697,216 S | 1/2014 | Chan et al. |
| 8,642,831 B2 | 2/2014 | Larsen et al. |
| 8,663,171 B2 | 3/2014 | Tambourgi et al. |
| D705,429 S | 5/2014 | Cheney et al. |
| D707,829 S | 6/2014 | Chan et al. |
| D708,751 S | 7/2014 | Chan et al. |
| 8,777,986 B2 | 7/2014 | Straehnz et al. |
| D712,045 S | 8/2014 | Thornton |
| D713,534 S | 9/2014 | Manley, Jr. |
| D713,967 S | 9/2014 | Adoni |
| D714,575 S | 10/2014 | Mah |
| 8,884,094 B2 | 11/2014 | Lockwood et al. |
| D718,812 S | 12/2014 | Sukhbaatar |
| 9,000,251 B2 | 4/2015 | Murphy et al. |
| RE45,510 E | 5/2015 | Hisamitsu |
| D728,803 S | 5/2015 | Sinda et al. |
| D745,688 S | 12/2015 | Chan et al. |
| D745,689 S | 12/2015 | Chan et al. |
| D746,479 S | 12/2015 | Arefieg |
| RE45,864 E | 1/2016 | Peron |
| D746,996 S | 1/2016 | Karlsson et al. |
| D750,789 S | 3/2016 | Mackay et al. |
| D757,950 S | 5/2016 | Karlsson et al. |
| 9,339,417 B2 | 5/2016 | Ogawa |
| 9,381,284 B2 | 7/2016 | Cornet et al. |
| 9,440,010 B2 * | 9/2016 | Locke ................ A61F 13/00 |
| 9,492,171 B2 | 11/2016 | Patenaude |
| 9,623,142 B2 | 4/2017 | Jonn et al. |
| D786,350 S | 5/2017 | Nakai et al. |
| D786,351 S | 5/2017 | Nakai et al. |
| D786,352 S | 5/2017 | Nakai et al. |
| D786,353 S | 5/2017 | Nakai et al. |
| D786,972 S | 5/2017 | Nakai et al. |
| 9,655,622 B2 | 5/2017 | Jonn et al. |
| D790,071 S | 6/2017 | Ahsani |
| D824,525 S | 7/2018 | Lacy et al. |
| D833,526 S | 11/2018 | Nakai et al. |
| 10,434,211 B2 | 10/2019 | Jonn et al. |
| 10,470,935 B2 | 11/2019 | Quintero |
| 2001/0002432 A1 | 5/2001 | Bugge |
| 2001/0028943 A1 | 10/2001 | Mashiko et al. |
| 2001/0037077 A1 | 11/2001 | Wiemken |
| 2002/0019652 A1 | 2/2002 | DaSilva et al. |
| 2002/0037310 A1 | 3/2002 | Jonn et al. |
| 2002/0039867 A1 | 4/2002 | Curro et al. |
| 2002/0185396 A1 | 12/2002 | Mainwaring et al. |
| 2002/0192107 A1 | 12/2002 | Hickey |
| 2002/0193721 A1 | 12/2002 | Vandruff |
| 2003/0031499 A1 | 2/2003 | Heard et al. |
| 2003/0093024 A1 | 5/2003 | Falleiros et al. |
| 2003/0100955 A1 | 5/2003 | Greenawalt et al. |
| 2003/0109819 A1 | 6/2003 | Tsuruda et al. |
| 2003/0125654 A1 | 7/2003 | Malik |
| 2003/0175824 A1 | 9/2003 | Pishko et al. |
| 2003/0220596 A1 | 11/2003 | Dunshee |
| 2003/0225355 A1 | 12/2003 | Butler |
| 2004/0001879 A1 | 1/2004 | Guo et al. |
| 2004/0060867 A1 | 4/2004 | Kriksunov et al. |
| 2004/0120849 A1 | 6/2004 | Stewart et al. |
| 2004/0142041 A1 | 7/2004 | MacDonald et al. |
| 2004/0162512 A1 | 8/2004 | Liedtke et al. |
| 2004/0220505 A1 | 11/2004 | Worthley |
| 2005/0015036 A1 | 1/2005 | Lutri et al. |
| 2005/0043820 A1 | 2/2005 | Browning |
| 2005/0085757 A1 | 4/2005 | Santanello |
| 2005/0147457 A1 | 7/2005 | Badejo et al. |
| 2005/0153090 A1 | 7/2005 | Marchitto et al. |
| 2005/0154340 A1 | 7/2005 | Schlussel |
| 2005/0182443 A1* | 8/2005 | Jonn ................ A61F 13/023 606/213 |
| 2005/0208100 A1 | 9/2005 | Weber et al. |
| 2005/0288706 A1 | 12/2005 | Widomski et al. |
| 2006/0058721 A1 | 3/2006 | Lebner et al. |
| 2006/0141012 A1 | 6/2006 | Gingras |
| 2006/0173394 A1 | 8/2006 | Stroock et al. |
| 2006/0265005 A1 | 11/2006 | Beese |
| 2007/0106195 A1 | 5/2007 | Marcoux et al. |
| 2007/0218101 A1 | 9/2007 | Johnson et al. |
| 2007/0272211 A1 | 11/2007 | Kassner |
| 2007/0299542 A1 | 12/2007 | Mathisen et al. |
| 2008/0051687 A1 | 2/2008 | Rogers |
| 2008/0154168 A1 | 2/2008 | Lutri |
| 2008/0086113 A1 | 4/2008 | Tenney et al. |
| 2008/0109034 A1 | 5/2008 | Mather et al. |
| 2008/0110961 A1 | 5/2008 | Voegele et al. |
| 2008/0167633 A1 | 7/2008 | Vannucci |
| 2008/0280037 A1 | 11/2008 | Sheridan et al. |
| 2008/0302487 A1 | 12/2008 | Goodman et al. |
| 2009/0074842 A1 | 3/2009 | Hsu |
| 2010/0106120 A1 | 4/2010 | Holm |
| 2010/0198161 A1 | 8/2010 | Propp |
| 2010/0262091 A1 | 10/2010 | Larsson |
| 2010/0298791 A1 | 11/2010 | Jones et al. |
| 2011/0047766 A1 | 3/2011 | McAulay et al. |
| 2011/0071415 A1 | 3/2011 | Karwoski et al. |
| 2011/0092874 A1 | 4/2011 | Baschnagel |
| 2011/0130699 A1 | 6/2011 | Madsen et al. |
| 2011/0208102 A1 | 8/2011 | Chawki |
| 2011/0253303 A1 | 10/2011 | Miyachi et al. |
| 2012/0220912 A1 | 8/2012 | Shang |
| 2012/0238933 A1 | 9/2012 | Murphy et al. |
| 2012/0277645 A1 | 11/2012 | Kikuta et al. |
| 2013/0012988 A1 | 1/2013 | Blume et al. |
| 2013/0041337 A1 | 2/2013 | Aali et al. |
| 2013/0066365 A1 | 3/2013 | Belson et al. |
| 2013/0084323 A1 | 4/2013 | Riebman et al. |
| 2013/0138068 A1 | 5/2013 | Hu et al. |
| 2013/0143326 A1 | 6/2013 | Tai et al. |
| 2013/0144399 A1 | 6/2013 | Tai et al. |
| 2013/0204077 A1 | 8/2013 | Nagale et al. |
| 2013/0218125 A1 | 8/2013 | Stopek et al. |
| 2013/0245784 A1 | 9/2013 | Tan et al. |
| 2013/0274717 A1 | 10/2013 | Dunn |
| 2013/0282049 A1 | 10/2013 | Peterson et al. |
| 2013/0317405 A1 | 11/2013 | Ha et al. |
| 2014/0024989 A1 | 1/2014 | Ueda |

(56) References Cited

U.S. PATENT DOCUMENTS

| | | |
|---|---|---|
| 2014/0107561 A1 | 4/2014 | Dorian et al. |
| 2014/0121649 A1 | 5/2014 | Calco |
| 2014/0155916 A1 | 6/2014 | Hodgkinson et al. |
| 2014/0171888 A1 | 6/2014 | Croizat et al. |
| 2014/0257348 A1 | 9/2014 | Priewe et al. |
| 2014/0257517 A1 | 9/2014 | Deichmann et al. |
| 2015/0057491 A1 | 2/2015 | Goddard et al. |
| 2015/0209186 A1 | 7/2015 | Abbott et al. |
| 2015/0257938 A1 | 9/2015 | Pensier |
| 2015/0297413 A1* | 10/2015 | Blanco .................. A61F 13/025 602/54 |
| 2015/0314114 A1 | 11/2015 | La Rosa |
| 2015/0351767 A1 | 12/2015 | Zoll et al. |
| 2016/0030248 A1 | 2/2016 | Potters |
| 2016/0045376 A1* | 2/2016 | Nielsen .................. A61F 13/025 602/55 |
| 2016/0089145 A1 | 3/2016 | Quintero et al. |
| 2016/0296673 A1 | 10/2016 | Sambusseti |
| 2017/0035422 A1 | 2/2017 | Belson et al. |
| 2017/0056568 A1 | 3/2017 | Shelton, IV et al. |
| 2017/0056569 A1 | 3/2017 | Vendely et al. |
| 2017/0189159 A1 | 7/2017 | Bartee et al. |
| 2017/0273837 A1 | 9/2017 | Brueckner |
| 2017/0367806 A1 | 12/2017 | Gingras et al. |
| 2018/0085103 A1 | 3/2018 | Quintero et al. |
| 2018/0085259 A1 | 3/2018 | Quintero |
| 2018/0085260 A1 | 3/2018 | Quintero |
| 2019/0381207 A1 | 12/2019 | Jonn et al. |

FOREIGN PATENT DOCUMENTS

| | | |
|---|---|---|
| CN | 201441532 U | 4/2010 |
| CN | 101965169 A | 2/2011 |
| CN | 102755216 A | 10/2012 |
| CN | 102781433 A | 11/2012 |
| CN | 203234898 | 10/2013 |
| CN | 204766892 U | 11/2015 |
| EP | 0532275 | 3/1993 |
| EP | 0730874 | 9/1996 |
| EP | 0746293 A1 | 12/1996 |
| EP | 1161212 | 8/2000 |
| EP | 2359782 | 8/2011 |
| EP | 2377498 | 10/2011 |
| EP | 2805698 | 11/2014 |
| EP | 3574875 A1 | 12/2019 |
| GB | 2078763 | 1/1982 |
| JP | 61-203020 | 12/1986 |
| JP | 62-87624 | 6/1987 |
| JP | 01-265967 | 10/1988 |
| JP | 2-140948 | 11/1990 |
| JP | 3-56429 U | 5/1991 |
| JP | 7-016258 | 1/1995 |
| JP | 2001-265967 | 9/2001 |
| JP | 1130927 S | 11/2001 |
| JP | 2002-537068 | 11/2002 |
| JP | 2003-153949 | 5/2003 |
| JP | 2004-24905 A | 1/2004 |
| JP | 2006-061263 | 3/2006 |
| JP | 3147394 U | 12/2008 |
| JP | 2009-022730 | 2/2009 |
| JP | 1359502 S | 5/2009 |
| JP | 2011-004850 | 1/2011 |
| JP | 1571238 S | 3/2017 |
| JP | 1629290 | 4/2019 |
| WO | WO 1983/002586 | 8/1983 |
| WO | WO 1995/004511 | 2/1995 |
| WO | WO 1996/040797 | 12/1996 |
| WO | WO 1998/026719 | 6/1998 |
| WO | WO 2000/049983 | 8/2000 |
| WO | WO 2004/049987 | 6/2004 |
| WO | 2005/007022 A2 | 1/2005 |
| WO | WO 2005/051259 | 6/2005 |
| WO | WO 2005/079674 | 9/2005 |
| WO | WO 2006/017109 | 2/2006 |
| WO | WO 2008/082444 | 7/2008 |
| WO | WO 2009/067062 | 5/2009 |
| WO | WO 2010/134873 | 11/2010 |
| WO | 2011152368 A1 | 12/2011 |
| WO | WO 2013/009725 | 1/2013 |
| WO | WO 2014/083570 | 6/2014 |
| WO | WO 2014/195710 | 12/2014 |
| WO | WO 2015/135351 | 9/2015 |

OTHER PUBLICATIONS

3M™ Steri-Strip Adhesive Closures Product Catalog Brochure, (2011) 8 pages.

3M™ Steri-Strip Adhesive Closures Product Catalog Brochure, (2012) 12 pages.

Allen, L.V. Jr et al Ansel's Pharmaceutical Dosage Forms and Drug Delivery Systems, 8th edition 2005 Lippincott Williams & Wilkins, Chapter 4, Dosage Form Design: Pharmaceutical and Formulation Considerations p. 131.

Ashley et al.: Further studies involving wound closure with a rapidly polymerizing adhesive; *Plastic and Reconstructive Surgery*; Apr. 1963; vol. 31; pp. 333-343.

Ashley et al.: Nonsutured closure of skin lacerations and nonsutured grafting of skin with a rapidly polymerizing adhesive; *Qtrly Bull. Northwestern University* (Evanston, Ill.) *Medical School*; 1962; vol. 36; pp. 189-194.

Bromberg et al.: Nonsuture fixation of split-thickness skin grafts; Surgery, Jun. 1964; vol. 55; pp. 846-853.

Cramer: Rapid Skin Grafting in Small Animals; *Plastic and Reconstructive Surgery and the Transplantation Bull*; Oct. 1962, vol. 30; pp. 149-150.

Cramer et al.: Autograft rejection induced by homografting. A phenomenon intermediate between homograft rejection and autoimmunity; *Plastic and Reconstructive Surgery*; Jun. 1965; vol. 35; pp. 572-587.

DeMaria, E. 'New skin closure system facilitates wound healing after cardiovascular implantable electronic device surgery' World Journal of Clinical Cases (2015) 3(8) pp. 675-677.

Dermabond Prineo Skin Closure Systems (22 cm) Brochure (2014), 7 pages.

Dermabond Prineo Skin Closure Systems (22 cm) Brochure (2015), 2 pages.

Healthcare Packaging. Advanced Wound Care Products and packaging Needs. Jun. 5, 2017 (earliest online date), [site visited May 8, 2018]. Available from the Internet, URL:https://www.healthcarepackaging.com/article/applications/healthcare/advanced-wound-care-products-and-packaging-needs> (Year: 2017).

Inou: Studies on the Surgical Use of Plastic Adhesive; *Am. Journal of Proctology*; 1962; vol. 13; pp. 219-226.

Jesse et al.: Fixation of split-thickness skin grafts with adhesive; *Plastic and Reconstructive Surgery*; Mar. 1964; vol. 33; pp. 272-277.

Kaplan: A technique of nonsuture wound closure with a plastic tissue adhesive; *Plastic and Reconstructive Surgery*; Feb. 1966; vol. 37(2); pp. 139-142.

Keddie et al.: Intrafollicular tinea versicolor demonstrated on monomer plastic strips; *Journal of Investigative Dermatology*; Sep. 1963; vol. 41; pp. 103-106.

Lazar, H.L. et al 'Novel Adhesive Skin Closures Improve Wound Healing Following Saphenous Vein Harvesting' J. Card Surg (2008) 23 pp. 152-155.

Leukosan SkinLink Application Guide (2006) 1 page.

Leukosan Skinlink. BSN Medical (2017) 1 page http://www.bsnmedical.com/products/wound%E2%80%90care%E2%80%90vascular/category%E2%80%90product%E2%80%90search/acute%E2%80%90wound%E2%80%90care/wound%E2%80%90closure/leukosanr%E2%80%90skinlink.html.

Pam Marketing Nut. Yikes! The Social Medica Quick Fix Band-Aids are Falling Off! Jul. 2012 [earliest online date], [site visited May 8, 2018]. Available from Internet, ,URL:http://www.pammarketingnut.com/2012/07/yikes-the-social-media-quick-fix-band-aids-are-falling-off/> (Year: 2012).

(56) References Cited

OTHER PUBLICATIONS

Parrish et al.: Synthetic resin adhesive for placement of skin grafts; *American Surgeon*; Nov. 1964; vol. 30; pp. 753-755.
Raekallio et al.: Acute reaction to arterial adhesive in healing skin wounds; *Journal of Surgical Research*; Mar. 1964; vol. 4; pp. 124-127.
Stone: Nonsuture closure of cutaneous lacerations, skin grafting and bowel anastomosis; *American Surgeon*; Mar. 1964; vol. 30; pp. 177-181.
TissuGlu Surgical Adhesive Patient Information Brochure. Cohera Medical, Inc. (2014) 6 pages.
TissuGlu FDA Summary of Safety and Effectiveness Data. Feb. 3, 2014 40 pages.
Topaz, M. et al 'The TopClosure 3S System, for skin stretching and a secure wound closure' Eur J Plast Surg (2012) 35 pp. 533-543.
TopClosure 3S System—Skin Stretching and Secure Wound Closure System Product Information Sheet (2010) 15 pages.
Wolfe et al.: The application of hydrostatic pressure to the burn injury, an experimental study: *Journal of Trauma: Injury Infections & critical Care*; May 1962; vol. 2; pp. 262-272.
ZipLine medical Zip Surgical Skin Closure Brochure (2013) 4 pages.
Communication received from the USPTO for co-pending U.S. Appl. No. 10/887,884 dated Aug. 11, 2006.
Communication received from USPTO for co-pending U.S. Appl. No. 10/779,721 dated Mar. 28, 2007.
Communication received from USPTO for co-pending U.S. Appl. No. 10/779,721 dated Apr. 16, 2007.
Communication received from the USPTO for co-pending U.S. Appl. No. 10/887,884 dated Mar. 6, 2008.
Communication received from the USPTO for co-pending U.S. Appl. No. 10/887,884 dated Dec. 12, 2008.
Communication received from the USPTO for co-pending U.S. Appl. No. 12/207,984 dated May 11, 2011.
Communication received from the USPTO for co-pending U.S. Appl. No. 12/163,021 dated May 13, 2011.
Communication received from the USPTO for co-pending U.S. Appl. No. 12/163,021 dated Feb. 2, 2012.
Communication received from the USPTO for co-pending U.S. Appl. No. 12/163,021 dated Jun. 22, 2012.
Communication received from the USPTO for co-pending U.S. Appl. No. 12/207,984 dated Jun. 28, 2012.
Communication received from USPTO for co-pending U.S. Appl. No. 12/163,021 dated Jun. 22, 2012.
Corrected International Search Report International Application No. PCT/US2005/004948 dated Jun. 22, 2005.
Extended European Search Report re: 14166813.7 dated Jul. 7, 2014.
In re the U.S. Appl. No. 12/163,021 the Non-Final rejection dated Aug. 14, 2013.
In re the U.S. Appl. No. 12/163,021 the Final rejection dated Jan. 3, 2014.
In re the U.S. Appl. No. 12/207,984 the Non-Final rejection dated Aug. 22, 2013.
In re the U.S. Appl. No. 12/207,984 the Final rejection dated Dec. 4, 2013.
International Preliminary Report on Patentability for International Application No. PCT/US2005/024042 dated Jan. 16, 2007.
International Search Report for International Application No. PCT/US2005/024042 dated May 12, 2006.
International Search Report for International Application No. PCT/US2005/004948 dated Jun. 9, 2009.
International Search Report re: PCT/US2015/051919 dated Apr. 14, 2016.
International Search Report re: PCT/US2017/052394 dated Nov. 21, 2017.
International Search Report re: PCT/US2017/052383 dated Dec. 6, 2017.
International Search Report re PCT/US2018/022842 dated Jun. 20, 2018.
International Search Report re PCT/US2018/022834 dated Jun. 22, 2018.
International Search Report re PCT/US2018/027790 dated Jun. 26, 2018.
Office action received from USPTO for co-pending U.S. Appl. No. 10/887,884 dated Apr. 25, 2006.
Office action received from USPTO for co-pending U.S. Appl. No. 10/779,721 dated Aug. 21, 2006.
Office action received from USPTO for co-pending U.S. Appl. No. 10/887,884 dated Oct. 12, 2006.
Office action received from USPTO for co-pending U.S. Appl. No. 10/779,721 dated Jan. 9, 2007.
Office Communication received from USPTO for co-pending U.S. Appl. No. 10/887,884 dated Jan. 22, 2007.
Office Action received from USPTO for co-pending U.S. Appl. No. 10/887,884 dated Feb. 1, 2007.
Office Action received from the USPTO for co-pending U.S. Appl. No. 12/163,021.
Office action received from USPTO for co-pending U.S. Appl. No. 10/779,721 dated Jul. 27, 2007.
Office Action received from USPTO for co-pending U.S. Appl. No. 10/887,884 dated Oct. 16, 2007.
Office Action received from USPTO for co-pending U.S. Appl. No. 10/887,884 dated Mar. 6, 2008.
Office action received from USPTO for co-pending U.S. Appl. No. 10/779,721 dated May 19, 2008.
Office action received from USPTO for co-pending U.S. Appl. No. 12/163,021 dated Jan. 9, 2010.
Office action received from USPTO for co-pending U.S. Appl. No. 12/163,021 dated Sep. 1, 2010.
Office action received from USPTO for co-pending U.S. Appl. No. 12/207,984 dated Sep. 1, 2010.
Office action received from USPTO for co-pending U.S. Appl. No. 12/163,021 dated Dec. 9, 2010.
Office action received from USPTO for co-pending U.S. Appl. No. 12/207,984 dated Dec. 9, 2010.
Office action received from USPTO for co-pending U.S. Appl. No. 12/163,021 dated May 13, 2011.
Office action received from USPTO for co-pending U.S. Appl. No. 12/163,021 dated Jul. 18, 2011.
Office action received from USPTO for co-pending U.S. Appl. No. 12/207,984 dated Aug. 1, 2011.
Office action received from USPTO for co-pending U.S. Appl. No. 12/163,021 dated Jan. 10, 2012.
Office action received from USPTO for co-pending U.S. Appl. No. 12/207,984 dated Jan. 17, 2012.
Office action received from USPTO for co-pending U.S. Appl. No. 12/207,984 dated Apr. 26, 2012.
Office action received from USPTO for co-pending U.S. Appl. No. 12/163,021 dated May 1, 2012.
Office action received from USPTO for co-pending U.S. Appl. No. 12/163,021 dated Sep. 17, 2012.
Office action received from USPTO for co-pending U.S. Appl. No. 12/207,984 dated Sep. 25, 2012.
Office action received from USPTO for co-pending U.S. Appl. No. 12/163,021 dated Aug. 14, 2013.
Office action received from USPTO for co-pending U.S. Appl. No. 12/207,984 dated Aug. 22, 2013.
Office action received from USPTO for co-pending U.S. Appl. No. 12/207,984 dated Dec. 4, 2013.
Office action received from USPTO for co-pending U.S. Appl. No. 12/163,021 dated Jan. 3, 2014.
Supplementary European Search Report for Application No. EP05769387 dated Jul. 9, 2009.
Supplementary European Search Report for Application No. EP05723162 dated Nov. 5, 2009.
Supplementary European Search Report for Application No. EP14166813 dated Jun. 30, 2014.
U.S. Appl. No. 09/430,177, filed Oct. 29, 1999.
U.S. Appl. No. 09/430,289, filed Oct. 29, 1999.
U.S. Appl. No. 09/430,180, filed Oct. 29, 1999.
U.S. Appl. No. 09/385,030, filed Aug. 30, 1999.
U.S. Appl. No. 09/176,889, filed Oct. 22, 1998.

(56) References Cited

OTHER PUBLICATIONS

U.S. Appl. No. 09/919,877, filed Aug. 2, 2001.
U.S. Appl. No. 10/779,721, filed Feb. 18, 2004.
Written Opinion re: PCT/US2015/051919 dated Apr. 14, 2016.
Written Opinion re: PCT/US2017/052394 dated Nov. 21, 2017.
Written Opinion re: PCT/US2017/052383 dated Dec. 6, 2017.
Written Opinion re: PCT/US2018/022842 dated Jun. 20, 2018.
Written Opinion re: PCT/US2018/027790 dated Jun. 26, 2018.
Written Opinion re PCT/US2018/022834 dated Jun. 22, 2018.
Dermabond Prineo Skin Closure System (22 cm) Fact Sheet. (2016) 2 pages.
JP 7040744,1995, English claims.
JP 3059327,1991, English claims.
Japanese Office Action dated Feb. 19, 2019 for Design Appln. No. 2018-017274.
Japanese Office Action dated Feb. 26, 2019 for Patent Appln. No. 515463.
Office action received from USPTO for U.S. Appl. No. 15/964,538 dated Oct. 25, 2018.
Office action received from USPTO for U.S. Appl. No. 15/964,538 dated Dec. 27, 2018.
Office action received from USPTO for U.S. Appl. No. 15/490,176 dated Feb. 4, 2019.
Office action received from USPTO for U.S. Appl. No. 15/452,126 dated Nov. 16, 2018.
Office action received from USPTO for U.S. Appl. No. 14/864,033 dated Nov. 26, 2018.
Office action received from USPTO for U.S. Appl. No. 15/467,239 dated Feb. 28, 2019.
Office action received from USPTO for U.S. Appl. No. 15/278,376 dated Sep. 11, 2018.
Office action received from USPTO for U.S. Appl. No. 15/278,376 dated Feb. 21, 2019.
Office action received from USPTO for U.S. Appl. No. 15/675,159 dated May 14, 2019.
N/A, "Scar nose & Rinoplasty Surgery—New Gel+Demo:Nose Silicone Gel Sheet (beige)www.newgelplus.com", www.youtube.com, 2012, pp. 1-3, Page Number.
N/A, "Silagen Silicone Sheeting Strips Review|the skin spot", www.youtube.com, 2017, pp. 1-3, Page Number.

* cited by examiner

SKIN CLOSURE DEVICES WITH SELF-FORMING EXUDATE DRAINAGE CHANNELS

The present disclosure relates to skin closure devices applied over a surgical incision and preferably secured by a polymerizable adhesive, with the devices capable of forming drainage channels for removal of wound exudates.

BACKGROUND

A number of devices and methods exist for closing skin or tissue having a surgical incision, opening, cut, wound, or dissection. With these devices, skin or tissue parts separated by the incision are approximated or brought into close proximity forming as narrow a gap as possible in the area of the surgical incision or cut, and then covered by an adhesively attached tape which holds the skin or tissue in closed apposed arrangement until wound healing occurs after which the tape is removed.

Commercially available DERMABOND® PRINEO® Skin Closure System comprises a mesh having a pressure sensitive adhesive and a polymerization initiator disposed on the mesh. The mesh is applied onto the skin over a wound, and a polymerizable cyanoacrylate-based adhesive is then applied on the mesh and bonds the mesh to the skin.

However, skin closure systems may benefit from means to enable removal and drainage of wound exudates for wounds closed using skin closure systems, when required. Because skin closure systems seal the wound tightly, it can be beneficial to relieve any exudate pressure buildup or minimize the onset of skin maceration when the amount of exudates is significant.

U.S. Patent Application Publication No. 20140107561 "COMPRESSIVE OXYGEN DIFFUSIVE WOUND DRESSINGS" discloses a wound dressing, comprising: an oxygen-diffusive substrate defining a contact surface; and, a hydrophilic absorbent material in fluid communication with at least one portion of a periphery of the oxygen-diffusive substrate, wherein at least one portion of the substrate is configured to press the contact surface against a wound surface.

U.S. Patent Application Publication No. 20130274717 "SURGICAL CAVITY DRAINAGE AND CLOSURE SYSTEM" discloses a surgical drain device comprising a plurality of drain tubes positioned with an adhesion matrix, the adhesion matrix having a wound conforming shape and comprising a plurality of apertures for tissue contact through the matrix, the drain tubes being removable from the device and the adhesion matrix comprising a biodegradable polymer.

U.S. Patent Application Publication No. 20050085757 "EXPANDABLE TEMPORARY ABDOMINAL CLOSURE" discloses an abdominal and thoracic closure system comprising: a sterilizable flexible sheet comprising: a peripheral portion attachable to skin or fascia about a wound; and a central expandable portion allowing expansion of the abdomen or thorax while providing a continuous covering of a wound in the abdomen by the flexible sheet.

U.S. Patent Application Publication No. 20130066365 "RAPID CLOSING SURGICAL CLOSURE DEVICE" discloses a wound closure device, comprising: a first adhesion patch configured for adhering to a patient's skin; a second adhesion patch configured for adhering to the patient's skin; the wound closure device having an open position with an approximately elliptical shaped opening formed between the first adhesion patch and the second adhesion patch and a closed position wherein the first adhesion patch and the second adhesion patch are held in close proximity to each other.

U.S. Pat. No. 8,884,094 "VACUUM BANDAGE PACKING" discloses a vacuum bandage connectable to a source of fluid and provided for use with a wound having a wound surface, the bandage comprising: a wound dressing member having a wound contacting surface, a top surface, a port configured for fluid communication with the source of fluid, holes in the wound contacting surface configured for communication with a wound surface of the wound, and a passageway between the port and the holes, and a pack adjacent the top surface of the wound dressing member and having an aperture positioned about the port.

U.S. Pat. No. 9,381,284 "SYSTEM AND METHOD FOR SEALING AN INCISIONAL WOUND" discloses a method for treating an incisional wound having incisional walls, the method comprising: fluidly coupling a conduit to a source of reduced pressure, the conduit having a first end for receiving reduced pressure and a second end; fluidly coupling a scaffold to the second end of said conduit for receiving the reduced pressure, wherein the scaffold is formed from sufficiently thin porous material having an internal manifold extending generally longitudinally between opposing surfaces of the scaffold, the internal manifold having a primary flow channel comprised of bioresorbable tubing; positioning the opposing surfaces of the scaffold between the incisional walls of the incisional wound; fluidly coupling the internal manifold to the second end of the conduit for receiving the reduced pressure; surgically closing the incisional wound to maintain the reduced pressure therein; and providing the reduced pressure through the conduit to the scaffold and the internal manifold for the incisional wound, whereby the scaffold induces tissue apposition between the incisional walls.

U.S. Patent Application Publication No. 20100298791 "METHODS AND APPARATUSES FOR THE TREATMENT OF WOUNDS WITH PRESSURES ALTERED FROM ATMOSPHERIC" discloses an altered pressure device for treating a wound in an encapsulated space delimited by a cover secured over a wound, the device comprising: (a) an altered pressure source communicating with the encapsulated space via a length of tubing coupled with the source; and (b) layered intermediate materials composed of at least one foam layer and a top layer that is not foam, said non-foam layer in contact with the cover, wherein the top layer comprises structural characteristics that provide efficient gas permeation into the encapsulated space when interfacing with the cover.

Skin closure devices and dressings having porated or porous or apertured tape structure can release the pressure of wound exudates and provide for drainage, however these systems will also leave the incision and wound open to ingress of contaminates through the pores or apertures, potentially resulting in infection. There continues to be a need for improved devices, systems, and methods for holding skin areas around the dissection in apposed arrangement and covered and isolated from ingress of contaminants, while still providing for drainage of exudates.

SUMMARY OF THE INVENTION

In one embodiment, the invention relates to a device for application onto incisions or wounds with a liquid rapidly polymerizable adhesive for forming skin closure systems, comprising a thin flexible flat porous tape, preferably a mesh, elongated along a longitudinal axis and having a lower side or wound-facing side and an opposing upper side, a periphery, and central portion in immediate vicinity of the axis; said mesh coated or impregnated with an initiator or accelerator of polymerization; said mesh having a plurality of elongated traces of soluble pressure sensitive adhesive (PSA) disposed on the wound-facing side; said traces covering from about 3% to about 50% of area of said tape and extending from central portion to the periphery of said tape.

According to another embodiment, a method is provided of using the device for application onto incisions or wounds with a liquid rapidly polymerizable adhesive for forming skin closure systems on a wound for skin incision closure, comprising the steps: positioning a device comprising soluble PSA disposed on the wound-facing side of the device; orienting the axis of the device in alignment with the incision ensuring the axis is approximately overlapping the incision; approximating edges of the incision to each other with the device and adhering the device to the skin; applying a polymerizable adhesive onto the upper side of the tape, allowing the adhesive to penetrate through the tape and contact the skin; allowing the adhesive to react with the initiator or accelerator of polymerization and polymerize thus bonding the tape to the skin; allowing exudate from the wound to at least partially dissolve the traces of soluble pressure sensitive adhesive (PSA) thus forming drainage channels; providing coverage of the incision and keeping the incision closed.

DETAILED DESCRIPTION

According to embodiments of the present invention, self-forming drainage channels are provided to remove exudates and allow drainage from the wound or surgical incision towards the periphery of the skin closure system.

Figure 1:
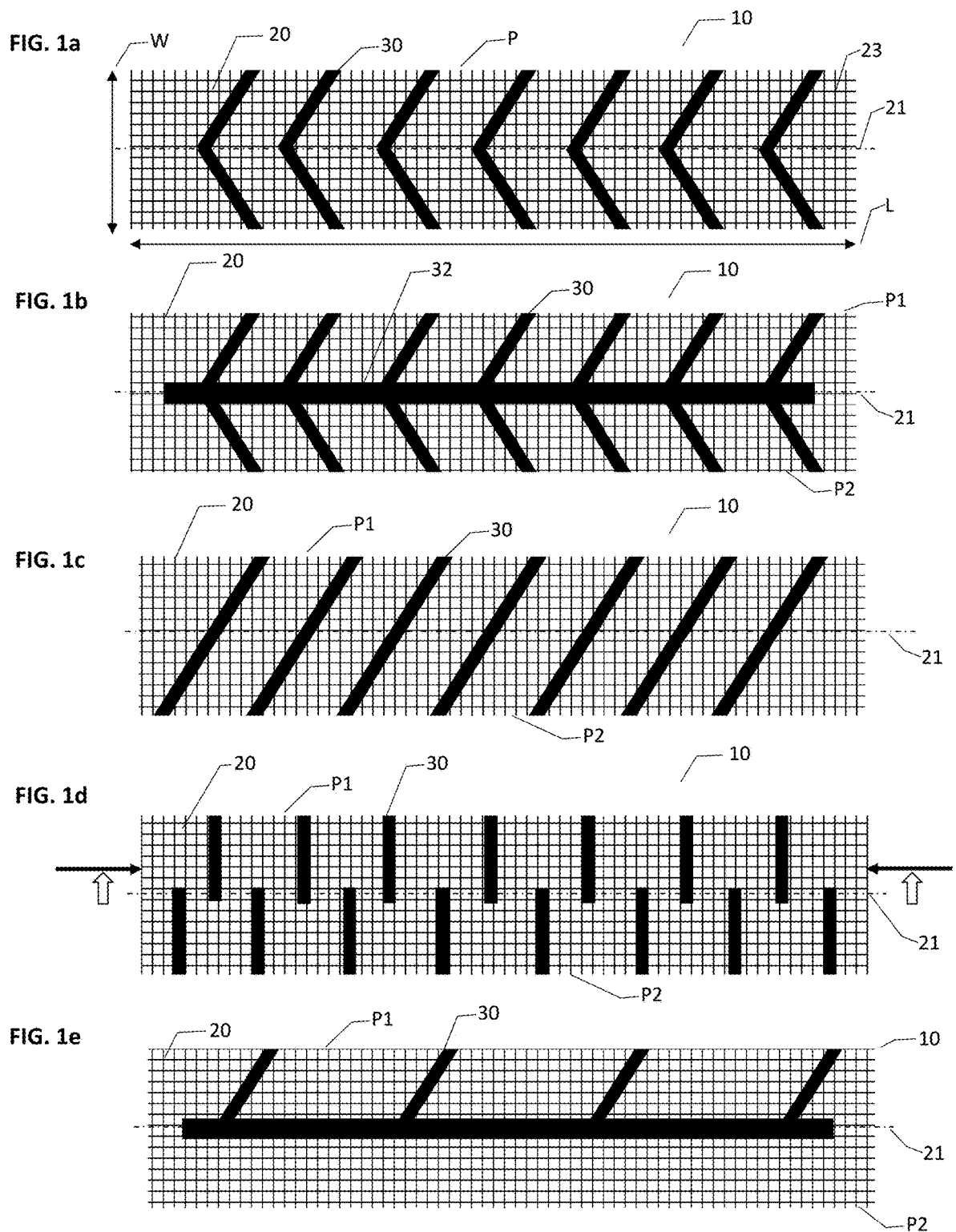
FIGS. 1a-e show embodiments of the skin closure device in schematic bottom views.

Referring now to FIGS. 1 a-e, embodiments of skin closure system device 10 are shown in a schematic view from a lower side 23, with device 10 comprising a thin, flat, flexible porous tape 20, (depicted as a mesh in all FIGS.) having length L and width W and elongated along longitudinal axis 21, with upper side 22 (not visible in views of FIG. 1 but visible for instance in FIG. 5) and lower or wound facing side 23. Tape 20 comprises a porous tape having perforations or micro-holes throughout and can be a woven, non-woven, extruded, punched, perforated, molded, etc. substrate. Preferably tape 20 is a mesh and coated and/or impregnated with an initiator or accelerator of polymerization.

On lower side 23, which is the tissue or skin facing side of device 10, there is a plurality of elongated traces 30 of soluble pressure sensitive adhesive (PSA), said traces covering from 3% to about 50% of the area of tape 20, more preferably 5% to 40%, such as 5%, 10%, 20%, and extending from a central portion to periphery P of tape 20, the central portion being in the immediate vicinity of axis 21. Soluble PSA traces 30 and 32 are configured to form channels for drainage of exudates as will be discussed below.

Traces 30 originate close to axis 21 and terminate at periphery P. Traces 30 can be in a form of linear segments of soluble PSA and can run under any angle to axis 21. As shown in FIG. 1a, traces 30 form an angle of about 60° to axis 21 in "V" shapes with the apex of "V" being at axis 21. Other angles are possible such as angles from 20° to 90°, such as 30°, 45°, 90°, and similar.

As shown in FIG. 1b, in one embodiment, there is provided soluble PSA trace 32 which runs along and at least partially overlaps axis 21, trace 32 also connected with all traces 30 in a "fishbone" arrangement.

As shown in FIG. 1c, in one embodiment, traces 30 comprise straight linear segments of soluble PSA and form a non-right angle to axis 21 running from upper periphery P1 to opposing lower periphery P2.

As shown in FIG. 1d, in one embodiment, traces 30 comprise straight linear segments of soluble PSA and form a right angle to axis 21 and runs from and overlaps the area of axis 21 area to upper periphery P1 in one direction and from axis 21 and overlapping with axis 21 to lower periphery P2 in the opposing direction.

As shown in FIG. 1e, in one embodiment, there is provided soluble PSA trace 32 which runs along and at least partially overlaps axis 21, trace 32 is also connected with all traces 30 which are only directed to upper periphery P1, with no traces 30 directed to lower periphery P2.

In preferred embodiments, at least a portion of traces 30 and/or 32 overlaps axis 21.

Figure 2:
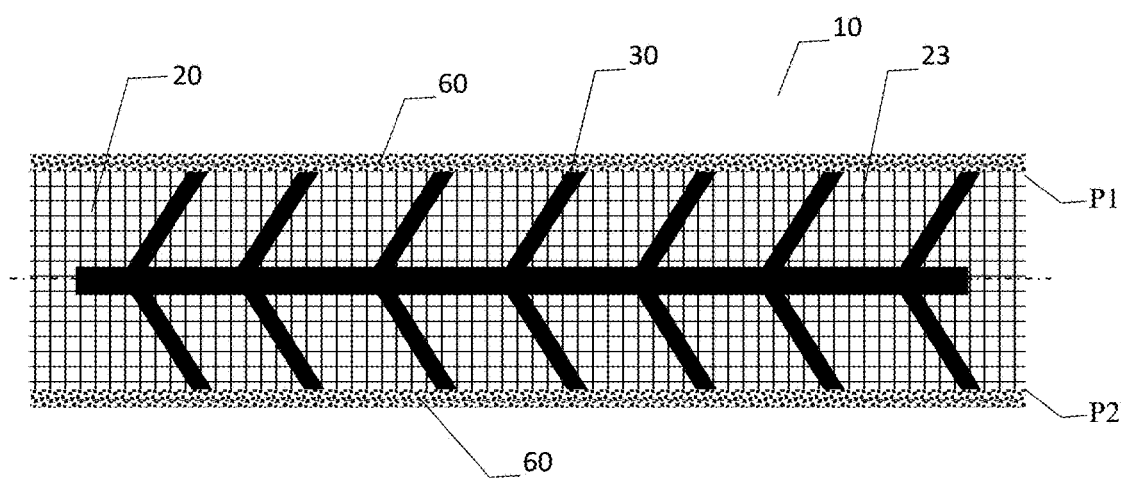
FIG. 2 shows an embodiment of the skin closure device in a schematic bottom view.

Referring now to FIG. 2, an embodiment of skin closure system device 10 is shown in a schematic view of wound-facing side 23, with elongated absorbent pads 60 attached to tape 20 at periphery P1 and P2 of tape 20. Absorbent pads 60 are configured to absorb exudates which are moving from the surgical incision or wound around axis 21 via drainage channels formed of soluble PSA traces 30 towards periphery P1 and P2. Absorbent pads 60 are made of any fluid-absorbing, biomedically compatible material and are in contact with at least some drainage channels formed of soluble PSA traces 30.

PSA Reinforcing Zones

Referring now to FIGS. 3a-d, embodiments of skin closure system device 10 are shown in a schematic view from wound-facing side 23, whereby in addition to soluble PSA traces 30 and 32, there are provided additional and optional PSA reinforcing zones 40, serving to improve attachment of device 10 to skin but not configured for forming drainage channels to remove exudates from central portions of device 10 around axis 21 to peripheries P1, P2 of device 10. PSA reinforcing zone 40 can be made of soluble PSA, similar to traces 30, 32, or of insoluble PSA. PSA reinforcing zones 40 can terminate at periphery P1, P2 (not shown) or at a distance from periphery P1, P2 (as shown).

Figure 3A:
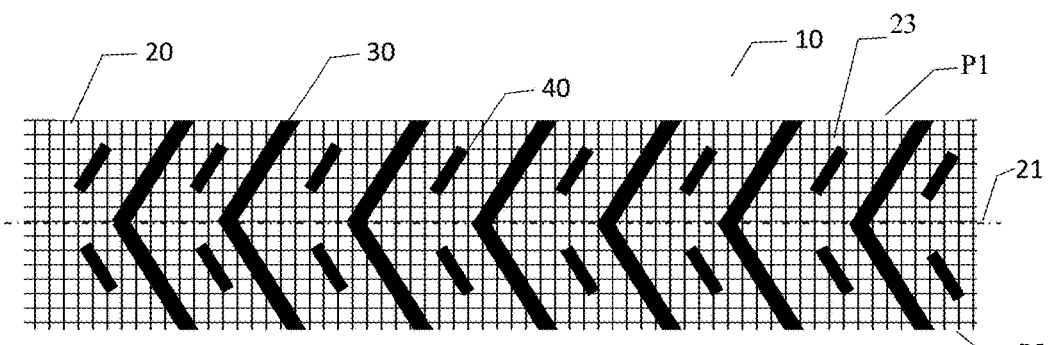
FIGS. 3a-d show embodiments of the skin closure device in schematic bottom views.
Figure 3B:
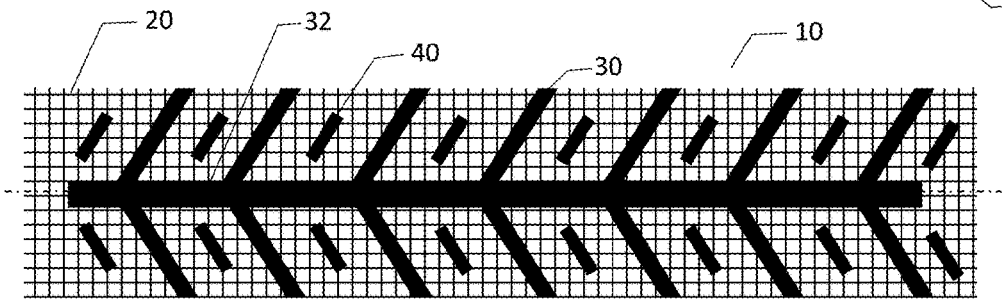
Figure 3C:
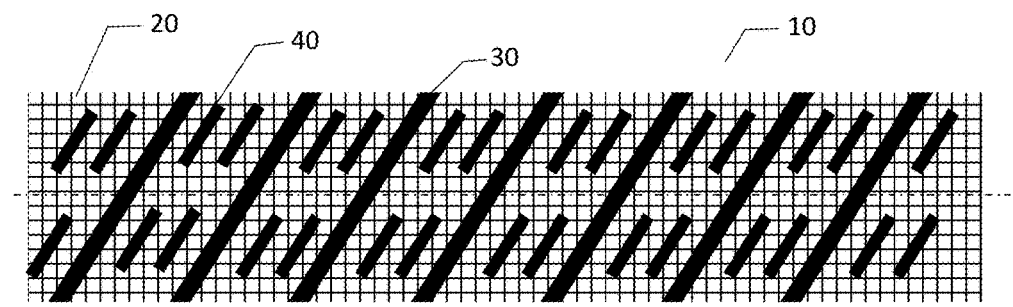

As shown in FIGS. 3a-c, PSA reinforcing zones 40 can comprise short linear segments of PSA positioned between traces 30 and not overlapping with axis 21 and traces 30, 32.

Figure 3D:
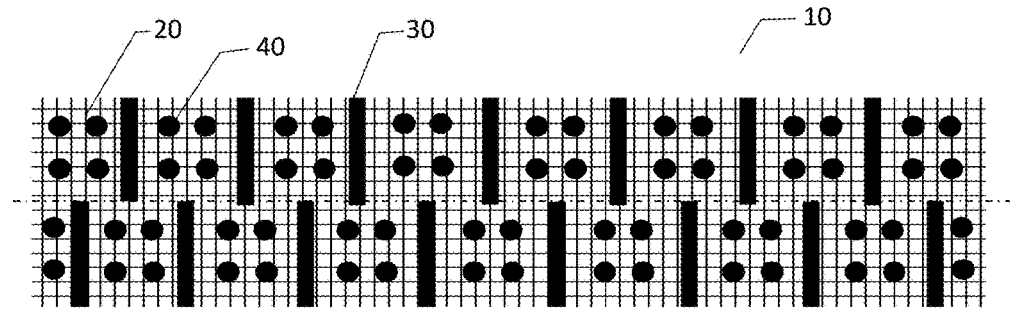

As shown in FIG. 3d, PSA reinforcing zones 40 can comprise non-linear shapes, such as circular or elliptical shapes, with segments of PSA positioned between traces 30 and not overlapping with axis 21 and traces 30, 32.

Figure 4A:
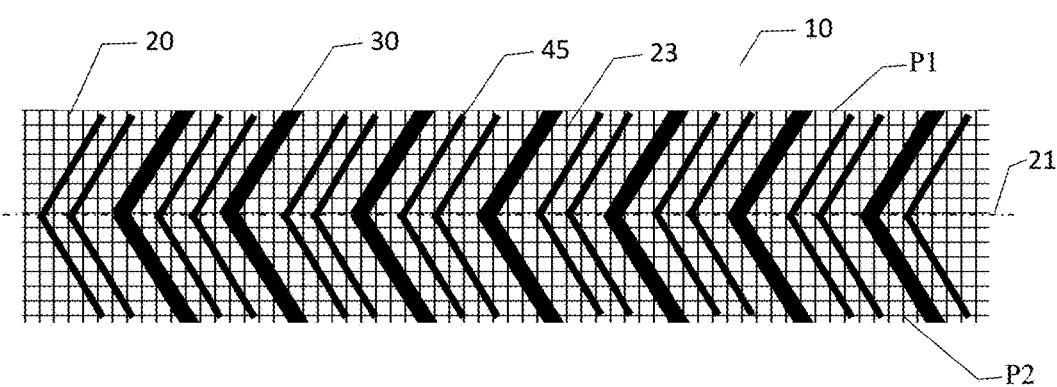
FIGS. 4a-b show embodiments of the skin closure device in schematic bottom views.
Figure 4B:
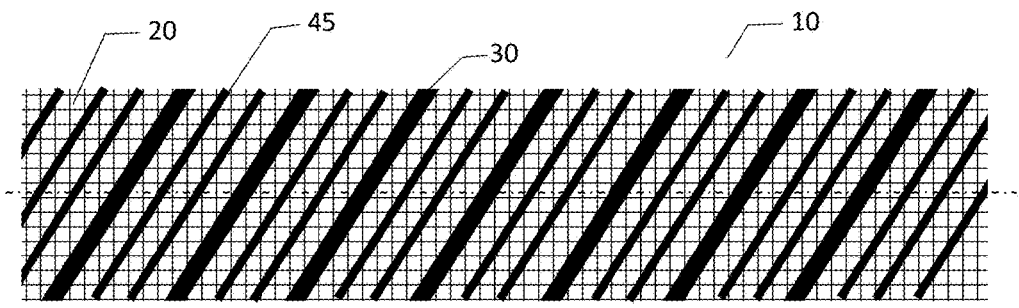

Referring now to FIGS. 4a-b, embodiments of skin closure system device 10 are shown in a schematic view from wound-facing side 23, whereby in addition to soluble PSA traces 30 and 32, there are provided additional PSA reinforcing zones 45, serving to improve attachment of device 10 to skin but not configured for forming drainage channels to remove exudates. PSA reinforcing zones 45 in these embodiments is made of insoluble PSA, with linear segments of insoluble PSA positioned between traces 30 and optionally aligned with but not overlapping with and not overlapping with traces 30, but optionally overlapping with axis 21. Insoluble PSA reinforcing zones 45 can terminate at periphery P1, P2 as shown in FIG. 4a-b or at a distance from periphery P1, P2 (not shown).

Optional PSA reinforcing zones 40, 45 may cover from 3% to about 50% of area of tape 20, more preferably 5% to 40%, such as 10%, 20%, 30%, 40%.

Soluble PSA traces 30 and 32 and optional PSA reinforcing zones 40, 45, in combination, may cover from about 5% to about 60% of area of mesh 20, more preferably 5% to 50%, such as 5%, 10%, 20%, 30%, 40%.

In Use

Figure 5A:
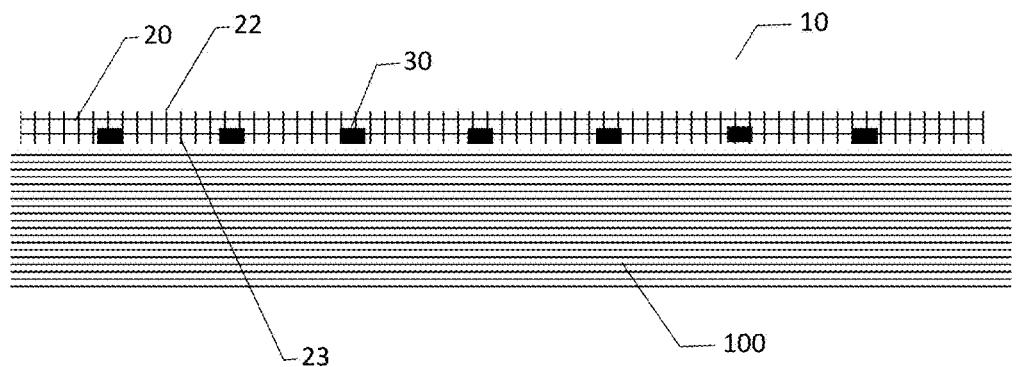
FIGS. 5a-c show embodiments of the skin closure device in schematic cross-sectional views during use of the device.
Figure 5B:
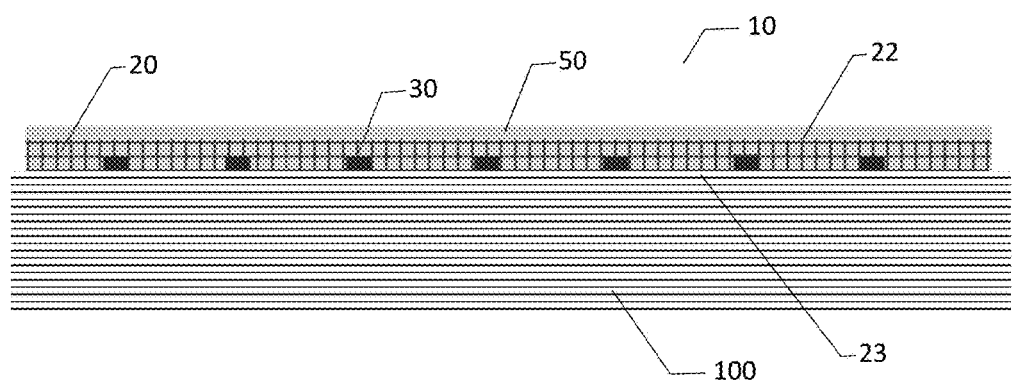
Figure 5C:
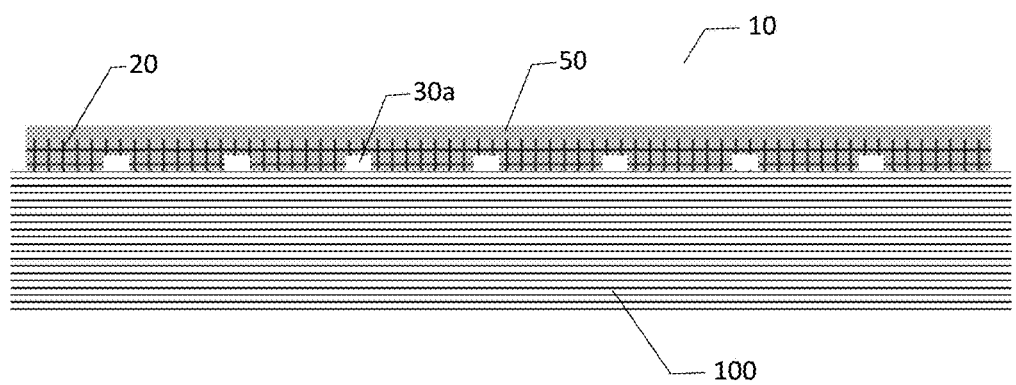

Referring now to FIGS. 5a-c, the embodiment of skin closure system device 10 of FIG. 1d is shown in a schematic cross-sectional side view as indicated by arrows on FIG. 1d. As shown in FIG. 5A, tape 20 is positioned on skin 100 having a wound or surgical incision (not shown) with lower side 23 on which traces of soluble PSA 30, 32 (not shown) are located, facing towards skin 100 and with opposing upper side 22 facing away from skin 100. Tape 20 is secured to skin by traces of soluble PSA 30, and also by optional traces of soluble PSA 32 (not shown), and also by optional traces of soluble or insoluble PSA 40, or insoluble PSA 45 (not shown).

Optionally, tape 20 is used to approximate and hold in apposition or close approximation the edges of surgical incision or wound, using traces of soluble PSA 30, optional traces of soluble PSA 32, and/or optional traces of soluble or insoluble PSA 40, or insoluble PSA 45 for securing tape 20 on skin 100 and for securing in close approximation or apposition the edges of surgical incision or wound.

The positioning of device 10 over the surgical incision or wound is performed so that axis 21 is as much as possible aligned with the surgical incision or wound and overlaps with the surgical incision or wound i.e., axis 21 is in registration the surgical incision or wound.

As shown in FIG. 5b, polymerizable or cross-linkable adhesive 50 is then uniformly applied over the whole of tape 20 upper surface 22, penetrating through tape 20 and establishing contact with skin 100. As shown, adhesive 50 does not contact skin 100 in the areas where soluble PSA 30 is present. Adhesive 50 can be expressed from a container having a porous tip impregnated with a polymerization or cross-linking accelerator or initiator. In a preferred embodiment, adhesive 50 is expressed from an applicator not having polymerization or cross-linking accelerator or initiator, with such polymerization or cross-linking accelerator or activator/initiator present on or in tape 20 in a releasable or reactive form, i.e., available for rapid reaction when contacted with adhesive 50.

Liquid adhesive 50 then polymerizes and/or cross-links and solidifies, establishing secure bond with skin 100 and tape 20. Advantageously, areas where traces of soluble PSA 30 are present are free of adhesive 50 being in contact with skin and tape 20 and it is in these areas that skin 100 only is only attached by traces of soluble PSA 30. Skin closure by device 10 is thus completed with surgical incision under tape 20 securely covered and closed.

As shown in FIG. 5c, in cases when exudates are forming at the site of surgical incision, these exudates will at least partially dissolve traces of soluble PSA 30. In these areas where traces of soluble PSA 30 have dissolved, channels 30a are formed in place of traces of soluble PSA 30, creating narrow pathways or channels between skin 100 and tape 20 impregnated and covered with adhesive 50. Thus channels 30a are self-forming due to dissolution of traces of soluble PSA 30, 32 by exudate and generally follow the direction of traces of soluble PSA 30, 32. Channels 30a are narrow pathways between skin 100 and mesh 20 covered with adhesive 50, with channels running under tape 20 and/or partially through tape 20.

Figure 6A:
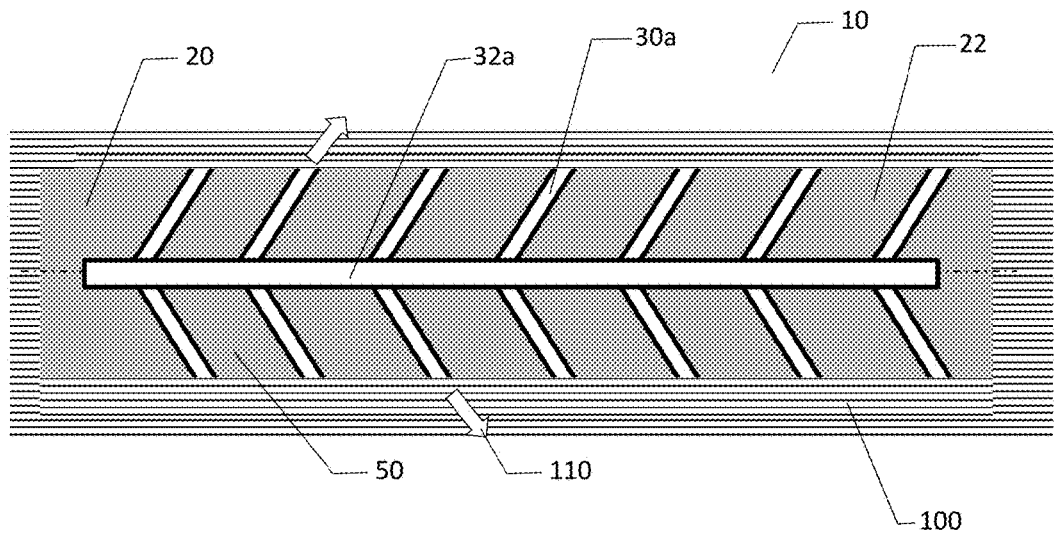
FIGS. 6a-b show embodiments of the skin closure device in schematic top views and illustrates formation of drainage channels.
Figure 6B:
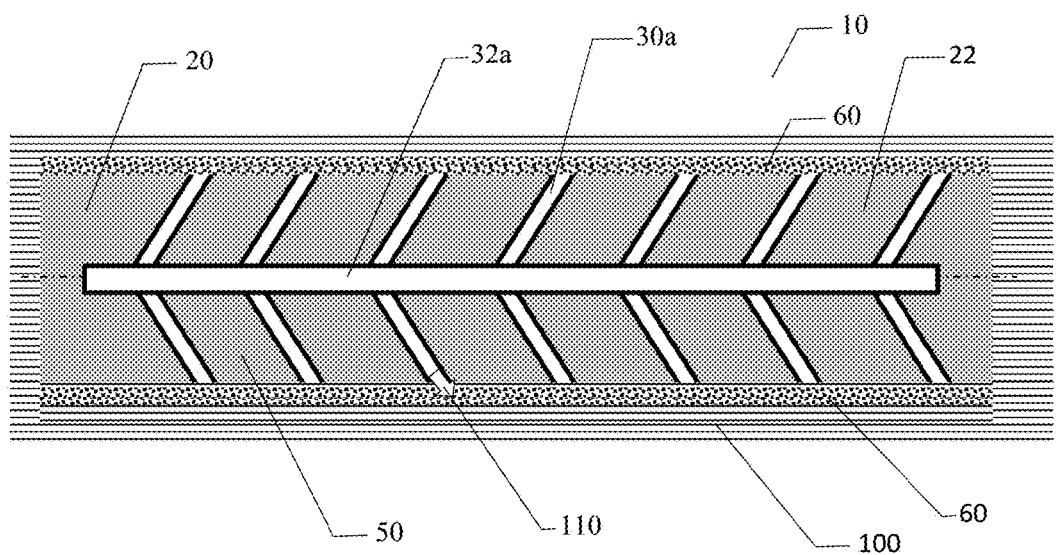

Referring now to FIGS. 6a-b, embodiments of device 10 are presented in a schematic top view from upper surface 22, after device 10 was applied to skin 100, adhesive 50 applied on top and solidified, binding tape 20 to skin 100, and after at least partial dissolution of traces of soluble PSA 30 and 32, thus forming drainage channels 32a along axis 21 (with axis 21 being approximately above surgical incision which is not shown) and drainage channels 30a running from the area around axis 21 and above and adjacent to the surgical incision towards periphery of device 10. FIG. 6a shows the embodiment of FIG. 1b with drainage channels 30a terminating at the periphery of device 10. FIG. 6b shows the embodiment of FIG. 2, with drainage channels 30a terminating at the periphery of device 10 at absorbent pads 60. Arrows 110 schematically illustrate the direction of exudate drainage from wound or incision areas adjacent axis 21 towards periphery of device 10.

Shielding Film Embodiments

Figure 7:
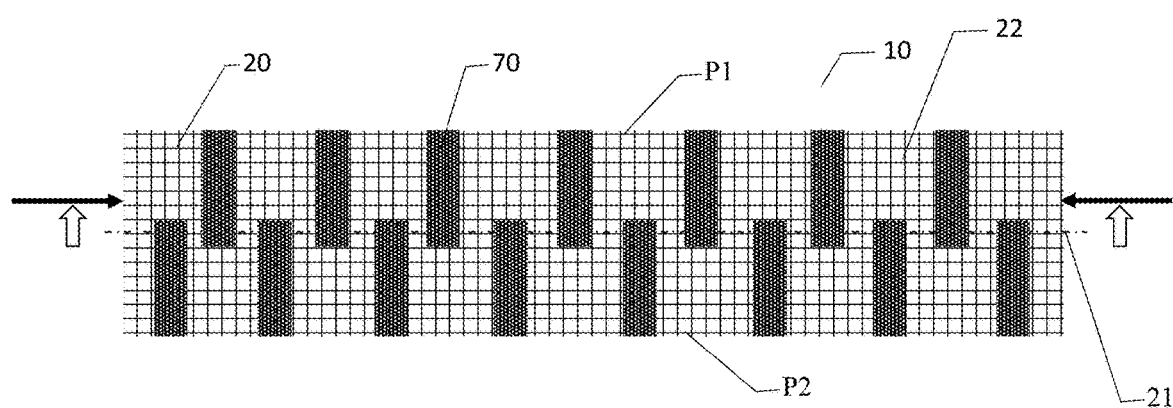
FIG. 7 shows an embodiment of the skin closure device in a schematic top view.

Referring now to FIG. 7, an alternative embodiment of device 10 is presented, showing view from upper side 22, whereby non-soluble shielding film traces 70 are attached to upper side 22 of tape 20. Non-soluble shielding film traces 70 may cover from 3% to about 60% of the top surface area of tape 20, more preferably 5% to 30%, and extending from periphery P of tape 20 to a central portion of tape 20, the central portion being in the immediate vicinity of axis 21. Shielding film traces 70 are configured to form channels for drainage of exudate by preventing the flow of polymerizable adhesive through tape 20 at film traces 70 and are configured in geometry and shapes similar to soluble PSA traces 30, 32 shown in FIGS. 1-4, inclusive. Shielding film traces 70 originate close to axis 21 and terminate at periphery P and can be in a form of linear segments of any polymeric or paper film and can run under any angle to axis 21, such as under angle to axis 21 and/or in "V" shapes with apex of "V" being at or near axis 21. In some embodiments, there is provided shielding film trace 70a (not shown) which runs along and at least partially overlaps axis 21, with such trace 70a also connected with all traces 70 in a "fishbone" arrangement. In one embodiment, shielding film traces 70 comprise straight linear segments of insoluble film, and run under a non-right angle to axis 21 running from upper periphery P1 to opposing lower periphery P2. In one embodiment, as shown in FIG. 7, shielding film traces 70 comprise straight linear segments of shielding film positioned at right angles to axis 21 and extending from axis 21 area and overlapping with axis 21 to upper periphery P1 in one direction and from axis 21 and overlapping with axis 21 to lower periphery P2 in opposing direction. In one embodiment (not shown), there is provided a shielding film trace 70a which runs along and at least partially overlaps axis 21, such trace 70a also connected with all shielding film traces 70 which are only directed to upper periphery P1, with no shielding film traces 70 directed to lower periphery P2.

In preferred embodiments, at least a portion of shielding film traces 70 overlap axis 21.

In one embodiment (not shown), elongated absorbent pads 60 are attached to at periphery P1 and P2 of tape 20. Absorbent pads 60 are configured to absorb exudate which are moving from the surgical incision or wound around axis 21 via drainage channels formed under shielding film traces 70 towards periphery P1 and P2.

Soluble PSA Traces

In some embodiments, soluble PSA traces 30, 32 are positioned in registration and alignment with non-soluble shielding film traces 70, 70a, with soluble PSA traces 30, 32 on lower side 23 immediately under corresponding shielding film traces 70, 70a on upper side 22 of tape 20. Shapes and arrangements of soluble PSA traces 30, 32 may be the same as shapes and arrangements of corresponding shielding film traces 70, 70a, with the same length but preferably with the width of shielding film traces 70, 70a being from 100% to 200% of the width of corresponding soluble PSA traces 30, 32, such as 100%, 120%, 150% of width of corresponding soluble PSA traces 30, 32.

PSA Reinforcing Zones

Embodiments of skin closure system device 10 are also disclosed whereby in addition to shielding film traces 70, 70a, there are provided additional and optional PSA reinforcing zones 40, 45, serving to improve attachment of device 10 to skin but not configured for forming drainage channels to remove exudate from central portions of device 10 around axis 21 to periphery P1, P2 of device 10. Similar in configurations to embodiments of FIGS. 3a-d, 4 PSA reinforcing zones 40 can be made of soluble PSA or of insoluble PSA and reinforcing zones 45 may be made of insoluble PSA. PSA reinforcing zones 40 can terminate at periphery P1, P2 or at a distance from periphery P1, P2. PSA reinforcing zones 40 can comprise short linear segments of PSA positioned between shielding film traces 70 and not overlapping with axis 21 and shielding ETH5907USNP 10 film traces 70. PSA reinforcing zones 40, 45 can comprise non-linear shapes, such as circular or elliptical shapes, with segments of PSA positioned between traces 30 and not overlapping with axis 21 and traces 30, 32.

In Use

The embodiments of skin closure system device 10 of FIG. 7 are shown in FIGS. 8a-d in a schematic cross-sectional side view as indicated by arrows in FIG. 7.

Figure 8A:
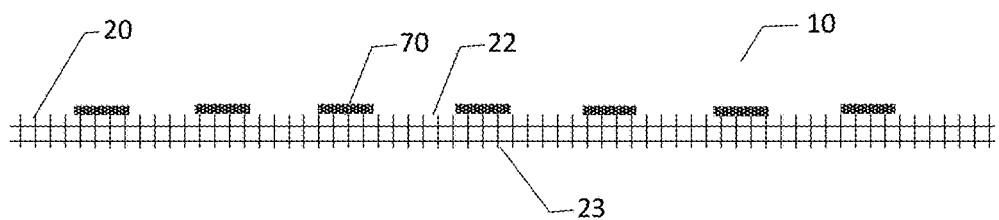
FIGS. 8a-d show embodiments of the skin closure device in schematic cross-sectional views during use of the device.

As shown in FIG. 8A, shielding film traces 70 are attached on upper side 22 of tape 20 and are configured to have width to prevent adhesive 50 penetrating into the areas immediately under shielding film traces 70. In this embodiment, there are no soluble PSA traces 30 disposed on tape 20, however there are traces of soluble or insoluble PSA 40 and insoluble PSA 45 (not shown) for securement of tape 20 to skin 100.

Figure 8B:
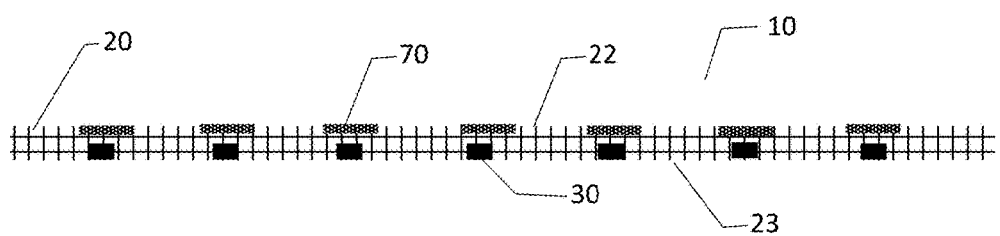

As shown in FIG. 8b, shielding film traces 70 are attached on upper side 22 of tape 20 and are in registration with soluble PSA traces 30 disposed on lower side 23 of tape 20, with shielding film traces 70 configured to have larger width vs. soluble PSA traces 30.

Figure 8C:
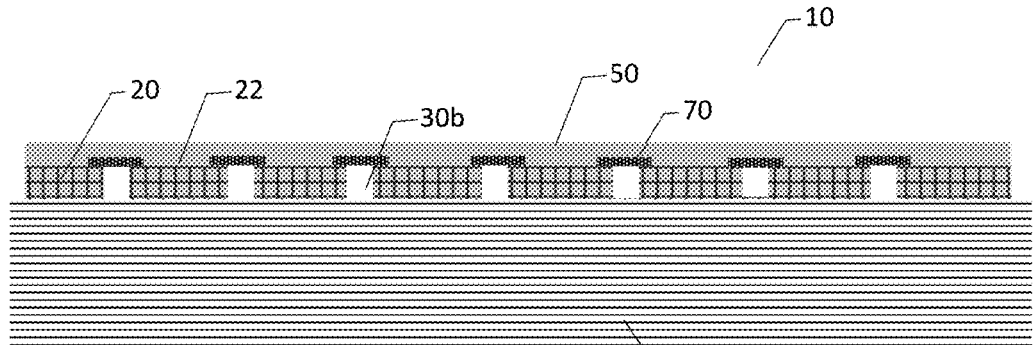
Figure 8D:
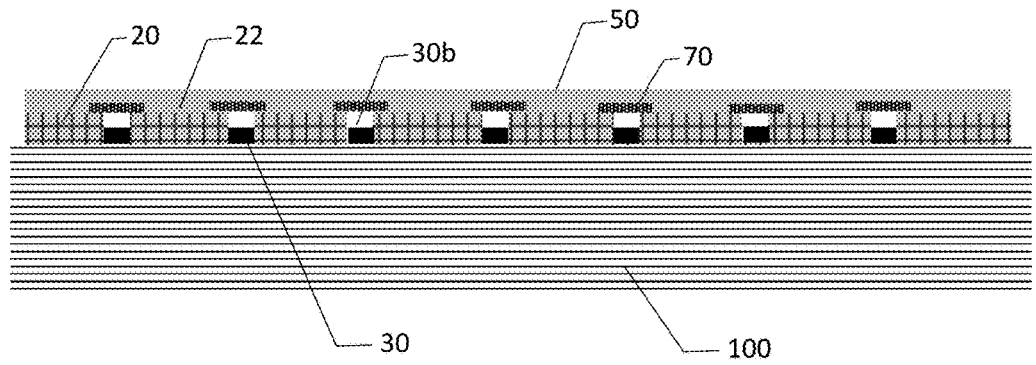

In use, and referring to FIGS. 8c and 8d, similarly to description of FIGS. 5a-c, tape 20 is positioned on skin 100 having a wound or surgical incision (not shown) with lower side 23 facing towards skin 100 and with opposing upper side 22 on which shielding film traces 70 are attached facing away from skin 100.

Tape 20 is secured to skin by optional traces of soluble PSA 30, and also by optional traces of soluble PSA 32 (not shown), and also by optional traces of soluble or insoluble PSA 40 or insoluble PSA 45 (not shown).

Optionally, tape 20 is used to approximate and hold in apposition or close approximation the edges of surgical incision or wound, using traces of soluble PSA 30, optional traces of soluble PSA 32, and/or optional traces of soluble or insoluble PSA 40 or insoluble PSA 45 for securing tape 20 on skin 100 and for securing in close approximation or apposition the edges of surgical incision or wound.

The positioning of device 10 over the surgical incision or wound is performed so that axis 21 is as much as possible aligned with the surgical incision or wound and overlaps with the surgical incision or wound i.e., axis 21 is in registration the surgical incision or wound.

As shown in FIG. 8c, whereby embodiment of FIG. 8a is presented in use, polymerizable or cross-linkable adhesive 50 is then uniformly applied over the whole mesh 20 upper surface 22, penetrating through tape 20 and establishing contact with skin 100. As shown, adhesive 50 does not contact skin 100 in the areas where shielding film traces 70 are present. Adhesive 50 can be expressed from a container having a porous tip impregnated with a polymerization or cross-linking accelerator or initiator. In a preferred embodiment, adhesive 50 is expressed from an applicator not having polymerization or cross-linking accelerator or initiator, with such polymerization or cross-linking accelerator or activator/initiator present on or in tape 20 in a releasable or reactive form, i.e., available for rapid reacting when contacted with adhesive 50.

Liquid adhesive 50 then polymerizes and/or cross-links and solidifies, establishing secure bond with skin 100 and mesh 20. Advantageously, areas where shielding film traces 70 are present are free of adhesive 50 being in contact with skin, with channels 30b forming under shielding film traces 70, creating narrow pathways or channels between skin 100 and tape 20 impregnated and covered with adhesive 50. Thus channels 30b are self-forming under shielding film traces 70. Channels 30b are narrow pathways between skin 100 and mesh 20 covered with adhesive 50, with channels 30b running under tape 20 and/or partially through tape 20.

As shown in FIG. 8d, whereby embodiment of FIG. 8b is presented in use, polymerizable or cross-linkable adhesive 50 is then uniformly applied over the whole of tape 20 upper surface 22, penetrating through tape 20 and establishing contact with skin 100. As shown, adhesive 50 does not contact skin 100 in the areas where shielding film traces 70 and soluble PSA 30 are present. Adhesive 50 can be expressed from a container having a porous tip impregnated with a polymerization or cross-linking accelerator or initiator. In a preferred embodiment, adhesive 50 is expressed from an applicator not having polymerization or cross-linking accelerator or initiator, with such polymerization or cross-linking accelerator or activator/initiator present on or in mesh 20 in a releasable or reactive form, i.e., available for rapid reacting when contacted with adhesive 50.

Liquid adhesive 50 then polymerizes and/or cross-links and solidifies, establishing secure bond with skin 100 and tape 20. Advantageously, areas where shielding film traces 70 and soluble PSA 30 are present are free of adhesive 50 being in contact with skin. Channels 30b are formed under shielding film traces 70 and upon dissolution of soluble PSA 30, as exudates forming at the site of surgical incision at least partially dissolve traces of soluble PSA 30, creating narrow pathways or channels between skin 100 and tape 20 impregnated and covered with adhesive 50. Thus channels 30b are self-forming under shielding film traces 70. Channels 30b are narrow pathways between skin 100 and tape 20 covered with adhesive 50, with channels 30b running under tape 20 and/or partially through tape 20.

Sizes/Dimensions

Tape 20 can be of any elongated shape to cover an articulating joint, such as elliptical, rectangular, and similar. Tape 20 can have ratio of length to width of about 1:2 to about 1:20, such as 1:5. The length of tape 20 is from about 10 cm to about 50 cm, such as 25 cm. The width of tape 20 is from 2 cm to 10 cm, such 3 cm, 5 cm.

Porosity of tape 20 is defined by size of pores or holes being from about 0.01 mm$^2$ to about 4 mm$^2$, more preferably 0.1 mm$^2$ to 1 mm$^2$. Percent of open area in tape 20, or ratio of area of holes to area of material surrounding holes is from about 95%-about 20%, more preferably 90%-40% constituting open area.

Elongated traces 30, 32 of soluble pressure sensitive adhesive (PSA) have width from about 0.5 mm to about 7 mm, more preferably 1 mm to 5 mm, such as 1, 1.5, 2, 3, 4 mm. The length of elongated traces 30 is from about 50% of the width of tape 20 to about 300% of the width of mesh 20, such as 10, 15, 20, 30, 40, 50, 60 mm. The length of elongated traces 32 is from about 50% to about 100% of the length of tape 20, such as 50, 100, 200, 300 mm.

PSA reinforcing zones 40, 45 can be linear, circular, elliptical curvilinear, etc. and having dimensions configured to fit between elongated traces 30, 32 of soluble pressure sensitive adhesive (PSA). Thickness or diameters of PSA reinforcing zones 40, 45 may range from 0.2 mm to 3 mm, such as 0.3, 0.4, 0.5, 1, 2 mm.

Non-soluble shielding film traces 70 have length similar to length of elongated traces 30, 32 of soluble pressure sensitive adhesive (PSA). The width of shielding film traces 70 may be equal or larger than the width of elongated traces 30, 32, such as 3 mm to about 10 mm, more preferably 3 mm to 6 mm, such as 3, 4, 5 mm.

PSA

Soluble PSA materials are exemplified by water soluble pressure sensitive adhesives, including Hydrocolloids; Homo-polymer Emulsion (PVA); Water-based Acrylic Adhesives; Polyurethane Dispersions PUDs; Poly ethylene glycol; Dextrin/Starch-Based Adhesives; N-vinyl caprolactam homopolymers; N-vinyl pyrrolidone copolymers; polyvinyl alcohol; cellulose ethers; methylcellulose; carboxymethylcellulose; polyvinylpyrrolidone; Polyvinyl Acetates.

Insoluble PSA materials are exemplified by water insoluble pressure sensitive adhesives, including Acrylic adhesives; Cyanoacrylate adhesives; Epoxy; Silicone based adhesives; and Urethane.

Initiator

In a preferred embodiment, initiators and/or accelerators or rate modifiers of adhesive polymerization or cross-linking can be releasably disposed on tape 20 or releasably incorporated into mesh 20. For example, one or more chemical substances may be dispersed in or on tape 20 such as being chemically bound, physically bound, coated, absorbed, or adsorbed to it.

For example, a polymerization initiator or accelerator or rate modifier may be loaded in or on tape 20 so that the initiator or rate modifier provides the desired initiation or rate modification effect to a subsequently applied polymerizable adhesive composition. The polymerization initiator or rate modifier may be immobilized in or on tape 20, so that the initiator or rate modifier does not become detached from tape 20 and its residues are dispersed in the resultant polymeric material. Alternatively, for example, the polymerization initiator or rate modifier may be initially attached to tape 20, but only in such a manner that it becomes mobilized or solubilized by a subsequently applied polymerizable adhesive composition and dispersed in the resultant polymeric material.

If desired, a combination of chemical substances may also be provided in or on tape 20, to provide multiple effects. For example, a first chemical species (such as a polymerization initiator or rate modifier) may be immobilized in or on tape 20, while a second, different chemical species (such as a bioactive material) may be detachably attached to tape 20. Other combinations of chemical species and resultant effects are also envisioned.

When present in or on tape 20, the chemical substances (i.e., polymerization initiator, rate modifier, and/or bioactive materials, or other additives), may be incorporated in or on tape 20 in any suitable manner. For example, the chemical substance may be added to tape 20 by contacting tape 20 with a solution, mixture, or the like including the chemical substances. The chemical substance may be added to tape 20, for example, by dipping, spraying, roll coating, gravure coating, brushing, vapor deposition, or the like. Alternatively, the chemical substance may be incorporated into or onto tape 20 during manufacture of tape 20, such as during molding.

The polymerization initiator or rate modifier loaded in or on tape 20 may provide a number of advantages for example, so as to provide faster polymerization time. The concentration of polymerization initiator or rate modifier may be increased to provide even faster polymerization time.

Because the polymerization initiator or rate modifier is loaded directly in or on tape 20, it is not necessary to mix the polymerizable adhesive composition with a polymerization initiator or rate modifier prior to application. This may allow a longer working time, where the polymerizable monomer composition may be more precisely and carefully applied over a longer period of time.

Such suitable initiators are known in the art and are described, for example, in U.S. Pat. Nos. 5,928,611 and 6,620,846, both incorporated herein by reference in their entireties, and U.S. Patent Application No. 2002/0037310, also incorporated herein by reference in its entirety. Quaternary ammonium chloride and bromide salts useful as polymerization initiators are particularly suitable. By way of example, quaternary ammonium salts such as domiphen bromide, butyrylcholine chloride, benzalkonium bromide, acetyl choline chloride, among others, may be used.

Benzalkonium or benzyltrialkyl ammonium halides such as benzyltrialkyl ammonium chloride may be used. When used, the benzalkonium halide may be benzalkonium halide in its unpurified state, which comprises a mixture of varying chain-length compounds, or it can be any suitable purified compound including those having a chain length of from about 12 to about 18 carbon atoms, including but not limited to C12, C13, C14, C15, C16, C17, and C18 compounds. By way of example, the initiator may be a quaternary ammonium chloride salt such as benzyltrialkyl ammonium chloride (BTAC).

Other initiators or accelerators may also be selected by one of ordinary skill in the art without undue experimentation. Such suitable initiators or accelerators may include, but are not limited to, detergent compositions; surfactants: e.g., nonionic surfactants such as polysorbate 20 (e.g., Tween20™ from ICI Americas), polysorbate 80 (e.g., Tween 80™ from ICI Americas) and poloxamers, cationic surfactants such as tetrabutylammonium bromide, anionic surfactants such as sodium tetradecyl sulfate, and amphoteric or zwitterionic surfactants such as dodecyldimethyl(3-sulfopropyl)ammonium hydroxide, inner salt; amines, imines and amides, such as imidazole, arginine and povidine; phosphines, phosphites and phosphonium salts, such as triphenylphosphine and triethyl phosphite; alcohols such as ethylene glycol, methyl gallate; tannins; inorganic bases and salts, such as sodium bisulfate, calcium sulfate and sodium silicate; sulfur compounds such as thiourea and polysulfides; polymeric cyclic ethers such as monensin, nonactin, crown ethers, calixarenes and polymeric-epoxides; cyclic and acyclic carbonates, such as diethyl carbonate; phase transfer catalysts such as Aliquat 336; organometallics such as cobalt naphthenate and manganese acetylacetonate; and radical initiators or accelerators and radicals, such as di-t-butyl peroxide and azobisisobutyronitrile.

Mixtures of two or more, such as three, four, or more, initiators or accelerators may be used. A combination of multiple initiators or accelerators may be beneficial, for example, to tailor the initiator of the polymerizable monomer species. For example, where a blend of monomers is used, a blend of initiators may provide superior results to a single initiator. For example, the blend of initiators can provide one initiator that preferentially initiates one monomer, and a second initiator that preferentially initiates the other monomer, or can provide initiation rates to help ensure that both monomer species are initiated at equivalent, or desired non-equivalent, rates. In this manner, a blend of initiators can help minimize the amount of initiator necessary. Furthermore, a blend of initiators may enhance the polymerization reaction kinetics.

Adhesive

In one embodiment, liquid or semi-liquid adhesive 50 is polymerized or is cross-linked polymerized or is cross-linked after coming in contact with initiators and/or accelerators of adhesive polymerization and/or cross-linking, including naturally found initiators on the tissue, such as moisture, traces of proteins, etc.

Such initiators and/or accelerators can be coated or disposed non-releasably, i.e. immobilized in or on the tape 20 while retaining activity to initiate or accelerate polymerization and/or cross-linking. In one embodiment, initiators and/or accelerators are disposed releasably, i.e., they can be at least partially released into and mix with flowing adhesive 50.

In a preferred embodiment, adhesive 50 is polymerized or is cross-linked after coming in contact with initiators and/or accelerators releasably disposed in or on tape 20. Rapid polymerization and/or crosslinking of adhesive 50 results in bonding of device 10 to tissue.

Adhesive 50 can be any type of biocompatible and rapidly cross-linkable and/or polymerizable compound or mixture of compounds. Rapidly cross-linkable and/or polymerizable means that after initiators or accelerators are added, or after the adhesive is formed from two or more components, it is capable of curing, i.e. cross-linking and/or polymerizing within 0.2 min to about 20 min, more preferably within 0.5 min to 10 min, such as 1, 2, 3, 5 min.

In one embodiment, adhesive 50 is formed prior to application onto tape 20, for instance by mixing two components contained in separate barrels or a two-barrel syringe, by passing these two components through a mixing tip. In this embodiment, there is no crosslinking initiator or accelerator disposed inside of mesh 20. In one embodiment, adhesive 50 is formed by mixing fibrinogen and thrombin together.

In one embodiment, adhesive 50 comprises fibrinogen, and crosslinking initiator or accelerator disposed inside of mesh 20 comprises thrombin.

In a preferred embodiment, the polymerizable adhesive composition may comprise a polymerizable monomeric adhesive. In embodiments, the polymerizable adhesive composition comprises a polymerizable 1,1-disubstituted ethylene monomer formulation. In embodiments, the polymerizable adhesive composition comprises a cyanoacrylate formulation. In embodiments, synthetic polymerizable adhesive materials such as polyurethane, polyethylene glycol, acrylates, glutaraldehyde and biologically based adhesives may be used.

Suitable .alpha.-cyanoacrylate monomers which may be used, alone or in combination, include alkyl .alpha.-cyanoacrylates such as 2-octyl cyanoacrylate; dodecyl cyanoacrylate; 2-ethylhexyl cyanoacrylate; butyl cyanoacrylate such as n-butyl cyanoacrylate; ethyl cyanoacrylate; methyl cyanoacrylate or other .alpha.-cyanoacrylate monomers such as methoxyethyl cyanoacrylate; 2-ethoxyethyl cyanoacrylate; 3-methoxybutyl cyanoacrylate; 2-butoxyethyl cyanoacrylate; 2-isopropoxyethyl cyanoacrylate; and 1-methoxy-2-propyl cyanoacrylate. In embodiments, the monomers are ethyl, n-butyl, or 2-octyl .alpha.-cyanoacrylate. Other cyanoacrylate monomers which may be used include alkyl ester cyanoacrylates, such as those prepared by the Knoevenagel reaction of an alkyl cyanoacetate, or an alkyl ester cyanoacetate, with paraformaldehyde, subsequent thermal cracking of the resultant oligomer and distillation.

Many other adhesive formulations can be used and are known to a skilled artisan. For example, mixtures containing PEG succinimidyl glutarate can be used as a flowable adhesive.

It should be understood that the foregoing disclosure and description of the embodiments of the present invention are illustrative and explanatory thereof and various changes in the size, shape and materials as well as in the description of the preferred embodiment may be made without departing from the spirit of the invention.

We claim:

1. A device for application onto incisions or wounds with a liquid rapidly polymerizable adhesive for forming skin closure systems, comprising:
   a thin flexible flat porous tape elongated along a longitudinal axis and having a lower side or wound facing side and an opposing upper side, a periphery, and central portion in immediate vicinity of the axis;
   said tape coated or impregnated with an initiator or accelerator of polymerization;
   said tape having a plurality of elongated traces of exudate soluble pressure sensitive adhesive (PSA) applied directly on the wound facing side;
   said traces covering from about 3% to about 50% of area of said tape and extending from the central portion and terminating at the periphery of said tape,
   wherein the traces are arranged in a pattern along a length of the tape to form drainage channels, and
   wherein a plurality of adhesive-impermeable elongated flat strips is disposed on the upper side of said tape, said strips extending from the central portion of said tape to the periphery of said tape, wherein said strips are registered with and are covering the traces of soluble PSA.

2. The device of claim 1, further comprising an elongated trace of soluble PSA disposed on the wound facing side which runs along and at least partially overlaps the axis covering the central portion of said tape.

3. The device of claim 1, further comprising at least one elongated absorbent pad attached to the tape at the periphery and configured to absorb exudates.

4. The device of claim 1, wherein said tape is further having a plurality of insoluble PSA reinforcing zones disposed on the wound facing side;
said zones not overlapping with said traces of soluble PSA.

5. The device of claim 4, wherein said tape has at least 40% of the tape not covered by the zones of insoluble PSA, traces of soluble PSA, or combination of both.

6. The device of claim 1, wherein the accelerator or the initiator comprises quaternary ammonium salt.

7. The device of claim 1 wherein the adhesive comprises cyanoacrylate monomers, fibrinogen, or PEG succinimidyl glutarate.

8. The device of any of the claim 1, 2, 3, 4, 5, 6 or 7 wherein the tape is a mesh.

9. A method of using the device of claim 1 on a wound for skin incision closure, comprising the steps:
positioning the device of claim 1 with the lower side facing the wound;
orienting the axis in alignment with the incision ensuring the axis is approximately overlapping the incision;
approximating edges of the incision to each other with the device of claim 1 and adhering the device of claim 1 to the skin;
applying a polymerizable adhesive onto the upper side of the tape, allowing the adhesive to penetrate through the mesh and contact the skin;
allowing the adhesive to react with the initiator or accelerator of polymerization and polymerize thus bonding the mesh to the skin; and
allowing exudates from the wound to at least partially dissolve the traces of soluble pressure sensitive adhesive (PSA) thus forming drainage channels.

10. A method of making the device of claim 1, comprising the steps:
coating the thin flexible flat porous tape with the initiator or accelerator of polymerization;
coating said tape on the wound facing side with the plurality of elongated traces of soluble pressure sensitive adhesive (PSA).

11. The method of claim 10, further comprising a step of coating said tape on the wound facing side with a plurality of insoluble PSA reinforcing zones disposed on the wound facing side;
said zones not overlapping with said traces of soluble PSA.

12. The method of claim 10, further comprising a step of applying the plurality of adhesive-impermeable elongated flat strips on the upper side.

13. A kit comprising:
the device of claim 1, and
a container with polymerizable adhesive having a tip for expressing and spreading said polymerizable adhesive onto the tape.

14. The kit of claim 13, wherein the tape is a mesh.

* * * * *